United States Patent [19]
Yoon

[11] Patent Number: 5,662,259
[45] Date of Patent: Sep. 2, 1997

[54] METHOD OF STAPLING ANATOMICAL TISSUE

[76] Inventor: InBae Yoon, 2101 Highland Ridge Dr., Phoenix, Md. 21131

[21] Appl. No.: 629,705

[22] Filed: Apr. 9, 1996

Related U.S. Application Data

[62] Division of Ser. No. 274,402, Jul. 13, 1994, Pat. No. 5,551,622.

[51] Int. Cl.⁶ .................................................. A61B 17/068
[52] U.S. Cl. ..................... 227/176.1; 227/19; 227/178.1; 227/180.1; 606/219
[58] Field of Search .................... 227/19, 175.1, 227/176.1, 179.1, 178.1, 180.1; 606/219

[56] References Cited

U.S. PATENT DOCUMENTS

| | | |
|---|---|---|
| 2,638,901 | 5/1953 | Sugarbaker . |
| 2,940,451 | 8/1960 | Vogelfanger et al. . |
| 2,965,900 | 12/1960 | Inokouchi . |
| 3,080,564 | 3/1963 | Strekopitov et al. . |
| 3,114,654 | 12/1963 | Nishiyama et al. . |
| 3,166,072 | 1/1965 | Sullivan, Jr. . |
| 3,176,896 | 4/1965 | Mallina . |
| 3,254,650 | 6/1966 | Collito . |
| 3,258,012 | 6/1966 | Nakayama et al. . |
| 3,388,847 | 6/1968 | Kasulin et al. . |
| 3,490,675 | 1/1970 | Green et al. . |
| 3,552,626 | 1/1971 | Astafiev et al. . |
| 3,589,589 | 6/1971 | Akopov . |
| 3,606,888 | 9/1971 | Wilkinson . |
| 3,638,652 | 2/1972 | Kelley . |
| 3,882,854 | 5/1975 | Hulka et al. . |
| 3,973,709 | 8/1976 | Akopov et al. . |
| 4,064,881 | 12/1977 | Meredith . |
| 4,198,982 | 4/1980 | Fortner et al. . |
| 4,216,890 | 8/1980 | Akopov et al. . |
| 4,242,902 | 1/1981 | Green . |
| 4,354,628 | 10/1982 | Green . |
| 4,466,436 | 8/1984 | Lee ........................................ 227/19 |
| 4,523,592 | 6/1985 | Daniel . |
| 4,548,202 | 10/1985 | Duncan . |
| 4,624,257 | 11/1986 | Berggren et al. . |
| 4,633,874 | 1/1987 | Chow et al. . |
| 4,749,114 | 6/1988 | Green . |
| 4,773,420 | 9/1988 | Green ........................................ 227/19 |
| 4,821,719 | 4/1989 | Fogarty . |
| 4,821,939 | 4/1989 | Green ........................................ 227/19 |
| 4,930,674 | 6/1990 | Barak ........................................ 227/19 |
| 5,015,249 | 5/1991 | Nakao et al. . |
| 5,040,715 | 8/1991 | Green et al. . |
| 5,049,153 | 9/1991 | Nakao et al. . |
| 5,074,454 | 12/1991 | Peters . |
| 5,156,609 | 10/1992 | Nakao et al. . |
| 5,156,614 | 10/1992 | Green et al. . |
| 5,158,567 | 10/1992 | Green . |
| 5,171,253 | 12/1992 | Klieman . |
| 5,222,961 | 6/1993 | Nakao et al. . |
| 5,242,457 | 9/1993 | Akopov et al. . |
| 5,258,008 | 11/1993 | Wilk . |
| 5,330,486 | 7/1994 | Wilk . |
| 5,346,115 | 9/1994 | Perouse et al. ........................................ 227/19 |
| 5,366,458 | 11/1994 | Korthoff et al. . |
| 5,376,095 | 12/1994 | Ortiz . |
| 5,484,451 | 1/1996 | Akopou et al. ........................................ 227/176.1 |

*Primary Examiner*—Scott A. Smith

[57] ABSTRACT

A method for a surgical stapler for applying multiple rows of surgical staples to biological tissue which includes a pair of opposed jaws adapted to receive tissue therebetween, a plurality of surgical staples and staple-forming anvils carried by each jaw in alignment with the staples and staple-forming anvils carried by the other jaw, and a mechanism for driving the tissue penetrating legs of the staples through the biological tissue and bending the legs against opposed anvils on the opposite side of the tissue to produce rows of finished surgical staples on both sides of the tissue being ligated. The staples and anvils in each of the jaws are arranged in spaced, parallel rows, with each row of staples being adjacent a row of anvils and adjacent rows of staples and anvils being either longitudinally staggered or aligned. Further, the staples and anvils are carried either alone or in combination in a pair of cartridges held by the opposed jaws, which are either linear or curved depending on the procedure to be performed with the surgical stapler.

9 Claims, 18 Drawing Sheets

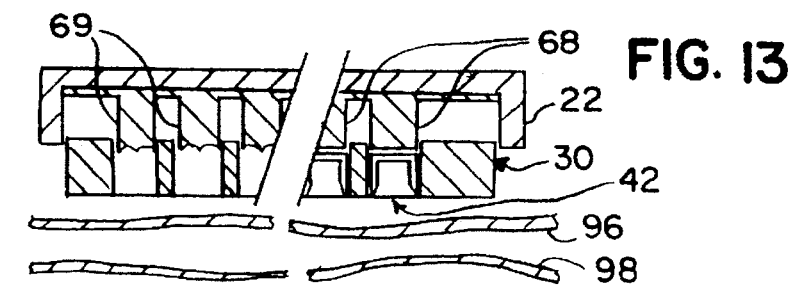
FIG. 13
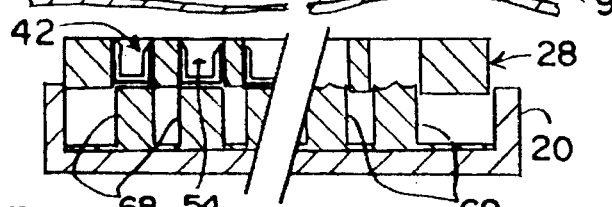
FIG. 14
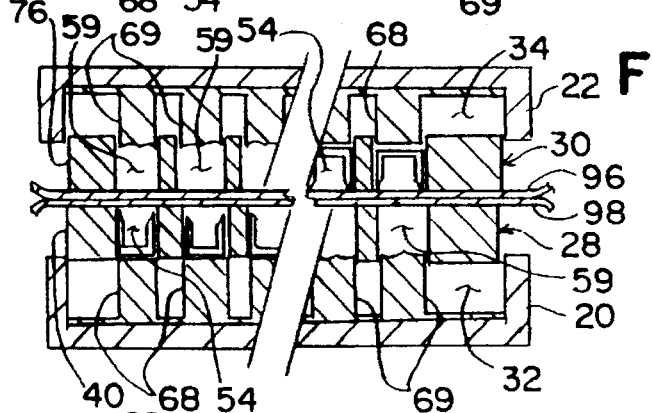
FIG. 15
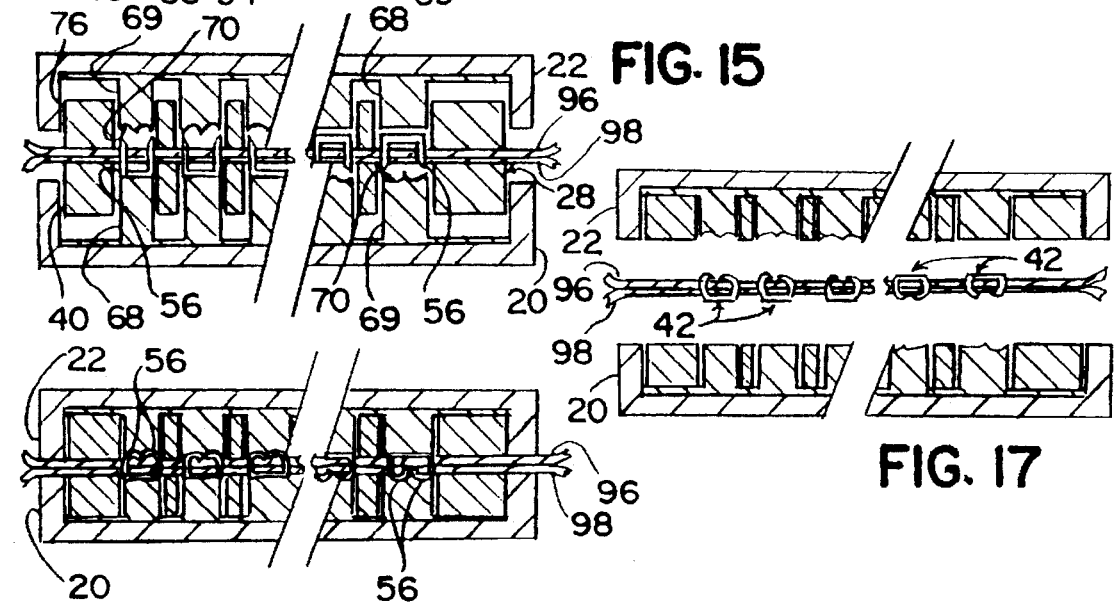
FIG. 17
FIG. 16

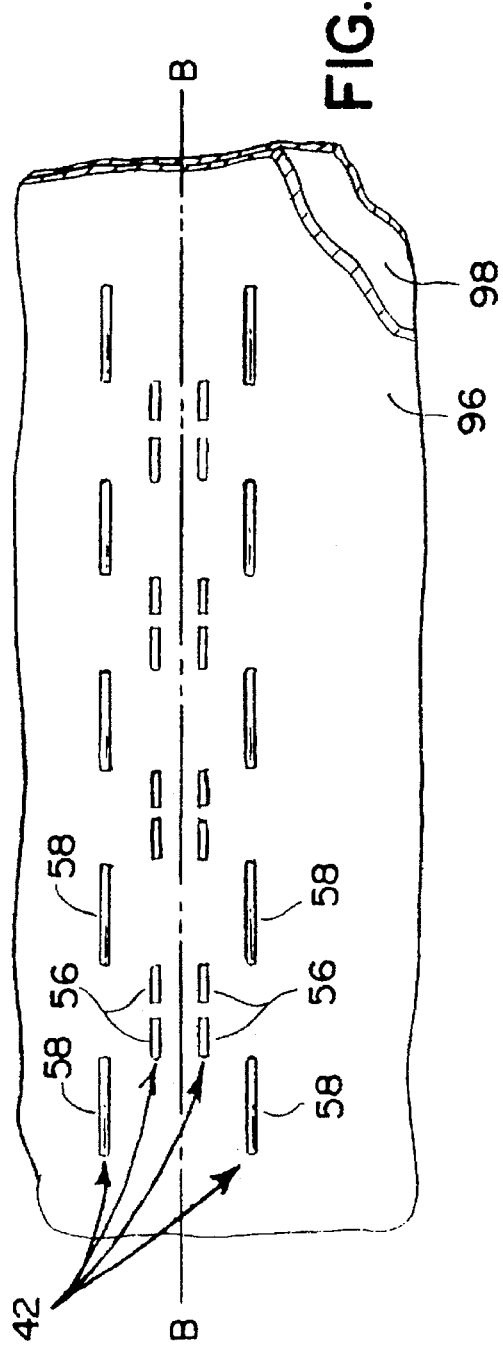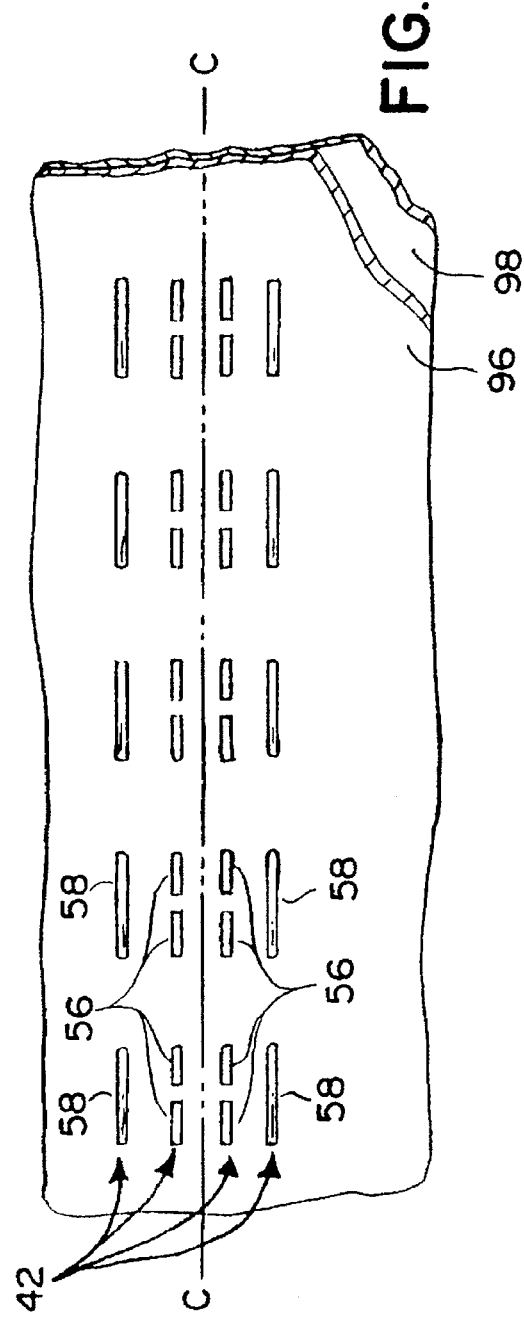

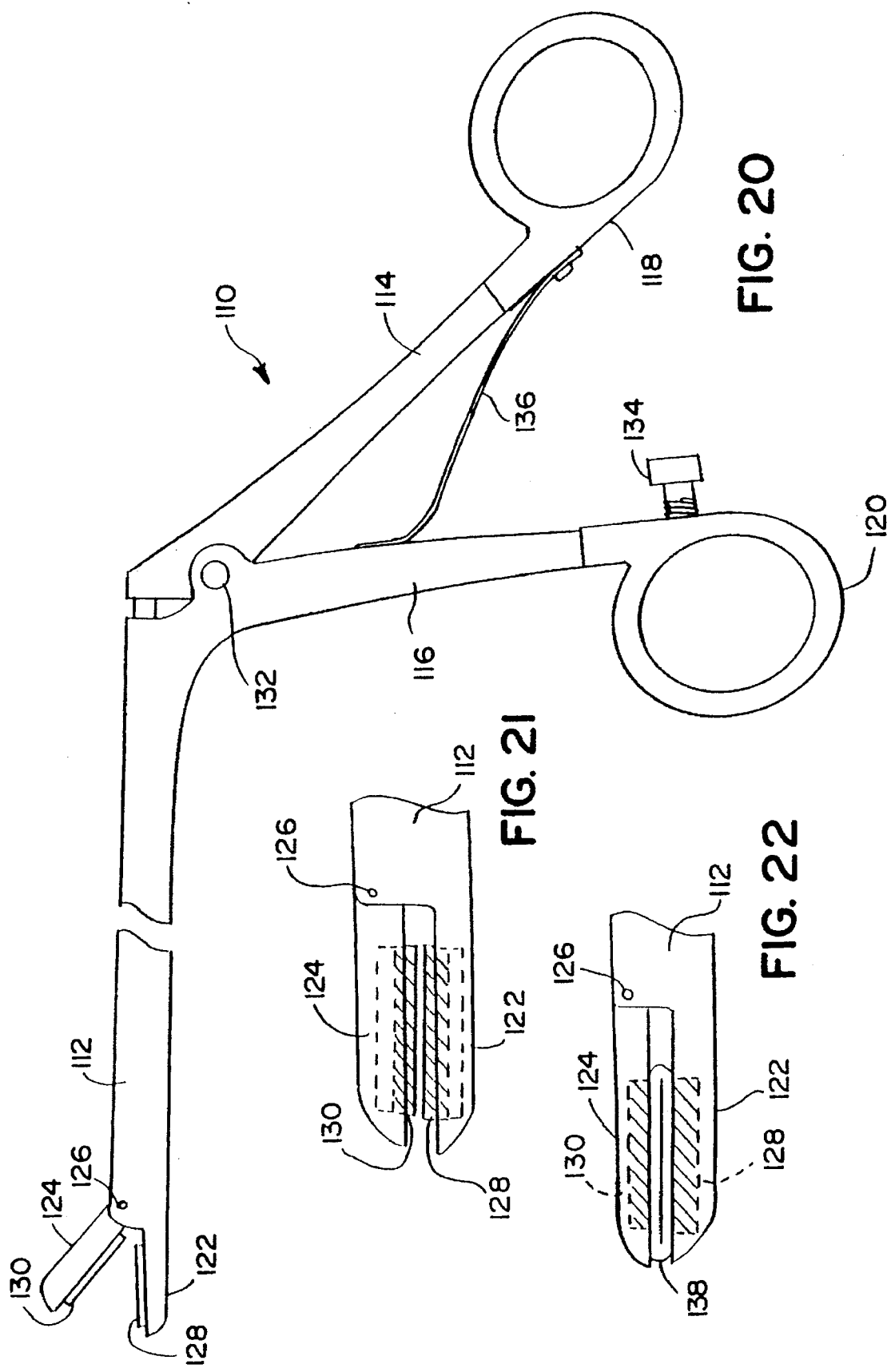

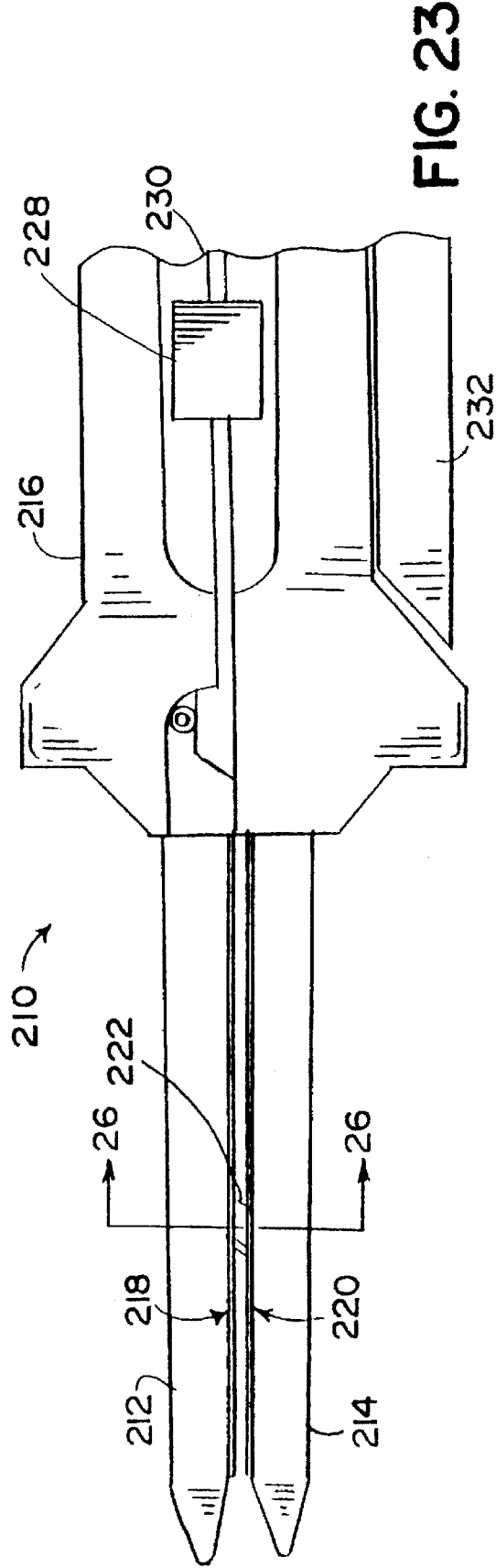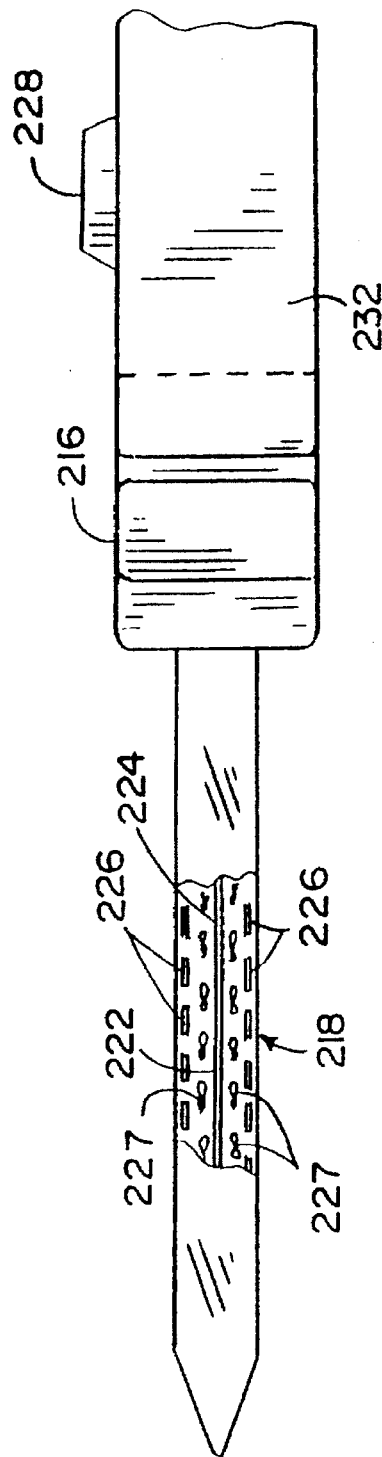

METHOD OF STAPLING ANATOMICAL TISSUE

This application is a division of patent application Ser. No. 08/274,402, filed Jul. 13, 1994, now U.S. Pat. No. 5,551,622.

BACKGROUND OF THE INVENTION

1. Field of the Invention

The present invention pertains to surgical stapling instruments and, more particularly, to surgical stapling instruments for applying a plurality of staples to body tissue in a substantially simultaneous manner.

2. Description of the Background Art

Suturing tissue and organs is a painstaking and time-consuming part of most surgical procedures. A high degree of skill is needed and the time and care required increases both the cost of surgery, the potential for excessive blood loss and the risk to the patient accompanying prolonged anesthetization. The advent of surgical staplers has facilitated the suturing process in many procedures, allowing uniform and consistent tissue-fastening to be accomplished with the squeeze of a handle or the advancement of a pusher bar after positioning the stapling instrument.

In some procedures, such as anastomosis (i.e., the joining of adjacent hollow organs), closely spaced parallel rows of sutures are required to seal fluid flow on either side of an incision. The capability of modern mass stapling instruments to apply several closely spaced parallel rows of staples has profoundly facilitated these and other procedures.

Mass staplers have evolved into two common forms. In one form, an instrument body has a U-shaped distal portion with a proximal movable jaw generally perpendicular to the instrument body and a distal anvil jaw fixedly or pivotably mounted to a lower portion of the movable jaw. Spaced parallel rows of distally directed staples are inserted into the movable jaw, tissue to be fastened is positioned between the jaws and the jaws are compressed against the tissue to a preset separation gap. A distal force is applied from the handle to drive movable pushers or hammers in the movable jaw distally forcing the staples out of the cartridge, through the tissue and into the anvil jaw where the staple legs are crimped to fasten the tissue. U.S. Pat. No. 3,080,564 to Strekopitor, et al., is exemplary of such staplers. Later developments resulted in the adaptation of the instrument to use preloaded replaceable cartridges to carry the staples instead of tediously reloading the movable jaw between uses. U.S. Pat. No. 3,589,589 to Akopov exemplifies such instruments. Fully disposable versions of this basic stapler form have been produced as well, primarily to avoid the work and cost associated with proper disassembly, sterilization and reassembly required for reuse.

The second common form of stapling instrument typically has a pair of elongate blunt-nosed jaws extending distally from the handle, one jaw holding a cartridge in which two or more rows of staples are held with the tissue penetrating staple legs aligned perpendicular to the opposite jaw face and the opposed jaw supporting rows of anvils with curved indentations aligned with the staple legs in the cartridge. These indentations bend and clinch the staple legs as the staples are driven into them. U.S. Pat. No. 3,490,675 to Green is exemplary of such stapling instruments. In use, the jaws of these instruments are positioned on either side of the tissue to be joined and then closed to a preset separation gap with the tissue held therebetween. A pusher bar, slidably mounted along the instrument body between the handle and the staple cartridge, is advanced distally into the staple carrying cartridge to individually cam driver bars, or hammers, which sequentially force the staples from the cartridge, into and through the tissue to be joined and into the anvils. Usually such instruments also incorporate a knife blade that is driven in tandem with the clinching of the staple legs to produce a clear cut in the tissue between linear rows of staples.

Other instruments apply two-piece surgical fasteners. These fasteners are typically made from biologically absorbable or non-absorbable polymeric materials which cannot maintain a bent or crimped configuration after being deformed. Hence, in addition to a tissue penetrating member having one or more prongs which are driven through one side of the tissue to be joined, such fasteners also require a retaining member which is positioned on the other side of the tissue to receive the prongs of the tissue penetrating member in an interlocking fashion. One such fastener structure and apparatus for applying it are disclosed in U.S. Pat. No. 5,156,614 to Green.

Unlike staples, two-piece polymeric fasteners require the fabrication of a plurality of differently designed components. Also, when utilizing two-piece fasteners, alignment between the tissue penetrating member and receiving member is critical. A concern with bioabsorbable two-piece fasteners, in particular, is whether they will have sufficient strength to hold the tissue together for a sufficient period of time to allow the tissue to heal prior to being absorbed.

Recently, the adaptation of a stapling instrument to laparoscopic and endoscopic procedures has appeared, as exemplified by U.S. Pat. No. 5,050,715 to Arein, et al. This apparatus includes an elongate tube-like body connecting a handle, positioned external to the surgical site, and two opposed jaws, aligned generally coaxially with the body and positionable at the surgical site. A cartridge of staples is carried in one of the jaws and the opposed jaw functions as an anvil. Tissue is clamped between the jaws, then staple driving bars are driven through the cartridge by a series of cam bars to sequentially force the staples through the tissue and into the anvil for clinching.

While prior art mass stapling devices are widely used, they suffer from many disadvantages when used in procedures requiring a secure constriction or ligation of bodily tissue. One of the disadvantages of prior art stapling instruments is that they suture the tissue to be joined from a single side only. Consequently, if some or all of the staples fail to pierce and/or crimp properly during the stapling procedure, layers of tissue may remain unconnected or at best weakly connected to the remaining tissue and prone to separating under tension. Even in fully formed complete staple installations the distribution of compression across and through the tissue is non-uniform as a result of this asymmetry. Another disadvantage of prior art staplers is that the stapler cannot apply rows of staples close to curved organs to minimize the amount of tissue suspended therefrom.

SUMMARY OF THE INVENTION

Accordingly, it is a primary object of the present invention to overcome the above mentioned disadvantages of the prior art and to provide a surgical stapler with staples and staple-forming anvils in each of two opposed jaws to apply surgical staples substantially simultaneously from both sides of the tissue being joined to securely ligate the tissue.

Another object of the present invention is to carry surgical staples in disposable cartridges held in opposed jaws of a surgical stapler to apply staples from both sides of the tissue being joined and to facilitate sterilization and reuse of the stapler.

A further object of the present invention is to stagger adjacent rows of staples and staple-forming anvils carried by opposed jaws of a surgical stapler to align the tissue penetrating legs of staples applied from one side of the tissue being joined with interstices between the webs of staples applied from the other side to better achieve hemostasis.

Yet another object of the present invention is to carry rows of spaced staples and staple-forming anvils on one or more curved jaws of a surgical stapler to apply staples along curved sections of tissue.

It is still another object of the present invention to ligate tissue with spaced parallel rows of surgical staples, with respective rows of staples being applied alternately from opposite sides of the tissue to achieve hemostasis.

Some of the advantages of the present invention over the prior art are that tissue stapling is initiated from both sides of the tissue to minimize failure of the suture and to more evenly distribute staple pressures across and through the ligated tissue, fluid seepage through the ligated tissue around the staples is reduced, the surgical instrument of the present invention can have the appearance, feel and operating action of traditional stapling instruments which are comfortable and well-known to the surgical community, stapling can be performed along curved lines and arcuate surfaces to better conform to the requirements of various procedures, the simplicity of construction of the present invention enables quick and inexpensive disassembly and sterilization, and the currently prevalent forms of stapling instruments can be readily adapted to incorporate the tissue-fastening improvements of the present invention.

The present invention is generally characterized in a surgical stapler having a pair of opposed jaws adapted to receive tissue therebetween, a plurality of staples and staple-forming anvils carried by each of the jaws, and operating means, coupled with the jaws, for driving tissue penetrating legs of the staples through the tissue and bending the legs against opposed anvils. The staples and anvils in each of the jaws are preferably arranged in spaced, parallel rows, with each row of staples being adjacent a row of anvils and adjacent rows of staples and anvils being either longitudinally staggered or aligned. In at least one embodiment, the staples and anvils are supported in a pair of cartridges carried by the opposed jaws of the stapler.

Another aspect of the present invention is characterized in a method of stapling biological tissue including the steps of positioning a plurality of staples and staple-forming anvils on both sides of the tissue, piercing the tissue from both sides with the tissue piercing legs of the staples, and bending the tissue piercing legs of the staples against the staple-forming anvils.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIGS. 13–17 are sequential cross-sectional views of the opposed jaws and staple cartridges taken through line 13—13 in FIG. 12 to illustrate use of the surgical stapler of the present invention, FIG. 18 is a top view of spaced, parallel rows of staples applied to body tissue from both sides of the tissue in a staggered arrangement.

FIG. 19 is a top view of spaced, parallel rows of staples applied to body tissue from both sides of the tissue in longitudinal alignment.

FIG. 20 is a side view of a surgical stapler according to the present invention for use in endoscopic procedures.

FIG. 21 is an enlarged view of the jaws of the surgical stapler of FIG. 20 in an intermediate position for insertion into an anatomical cavity.

FIG. 22 is an enlarged view of the jaws of the surgical stapler of FIG. 20 fully compressed.

FIG. 23 is a side view of a surgical stapler according to the present invention for making linear cuts between rows of finished staples.

FIG. 24 is a bottom view, partly in section of the surgical stapler of FIG. 23.

DESCRIPTION OF THE PREFERRED EMBODIMENTS

Figure 1:
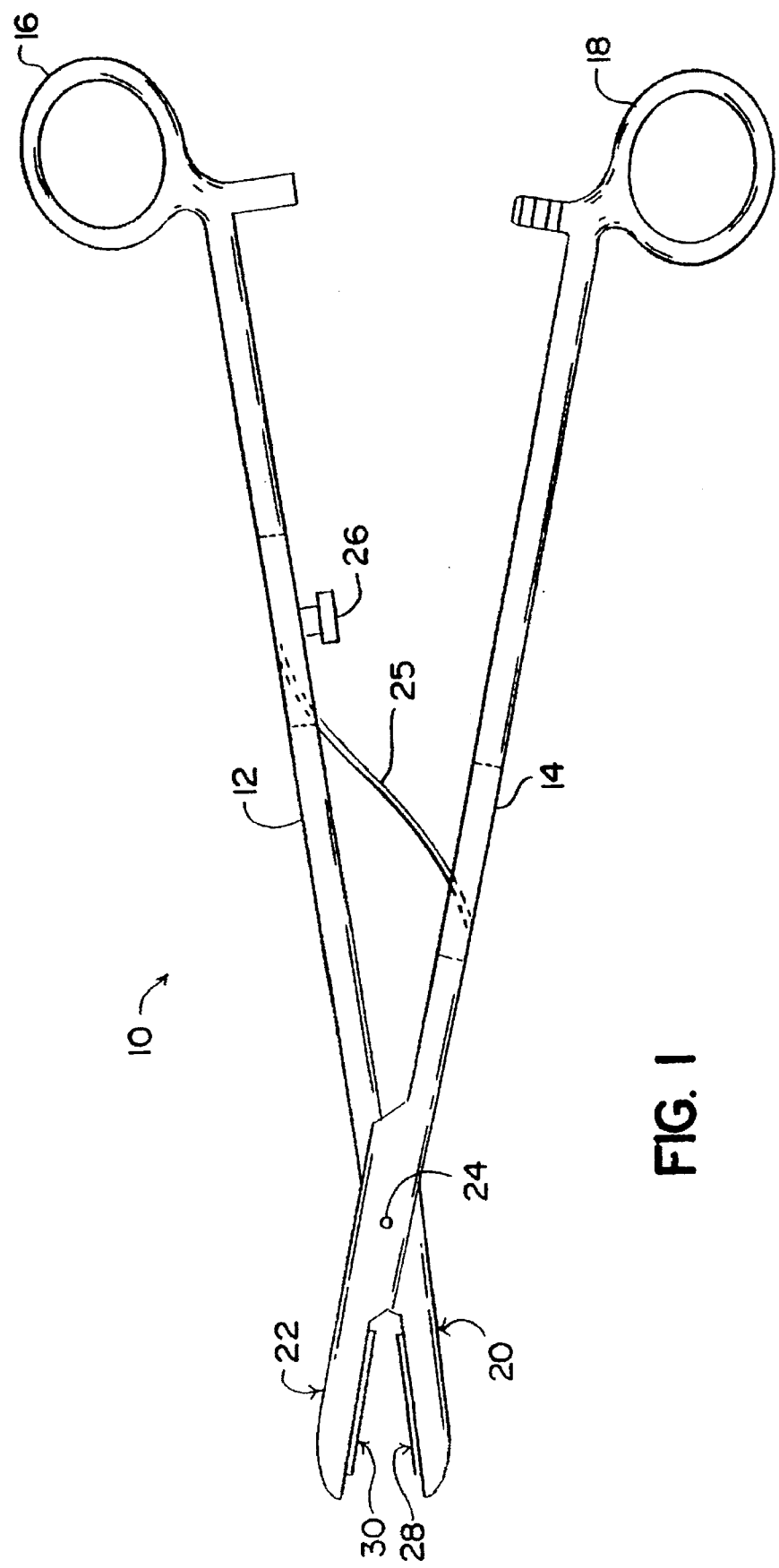
FIG. 1 is a side view of a surgical stapler according to the present invention.

A surgical stapler 10 according to the present invention is shown in FIG. 1. The stapler 10 includes a pair of legs 12 and 14 having at respective proximal ends thereof loop handles 16 and 18 sized to accommodate the thumb and one or more fingers of the hand, and first and second opposed jaws 20 and 22 at respective distal ends thereof configured to receive staple cartridges 28 and 30, respectively. The legs 12 and 14 are pivotably connected by a fulcrum pin 24, or the like, at a position intermediate loop handles 16 and 18 and opposed jaws 20 and 22. A leaf spring 25 extends between legs 12 and 14 to urge the two apart, and is positioned behind the fulcrum pin 24 and forward of a gap spacer 26 which protrudes from leg 12 toward leg 14 to limit the travel of the legs toward each other and consequently to establish a minimum gap distance between the opposed jaws 20 and 22.

Figure 2:
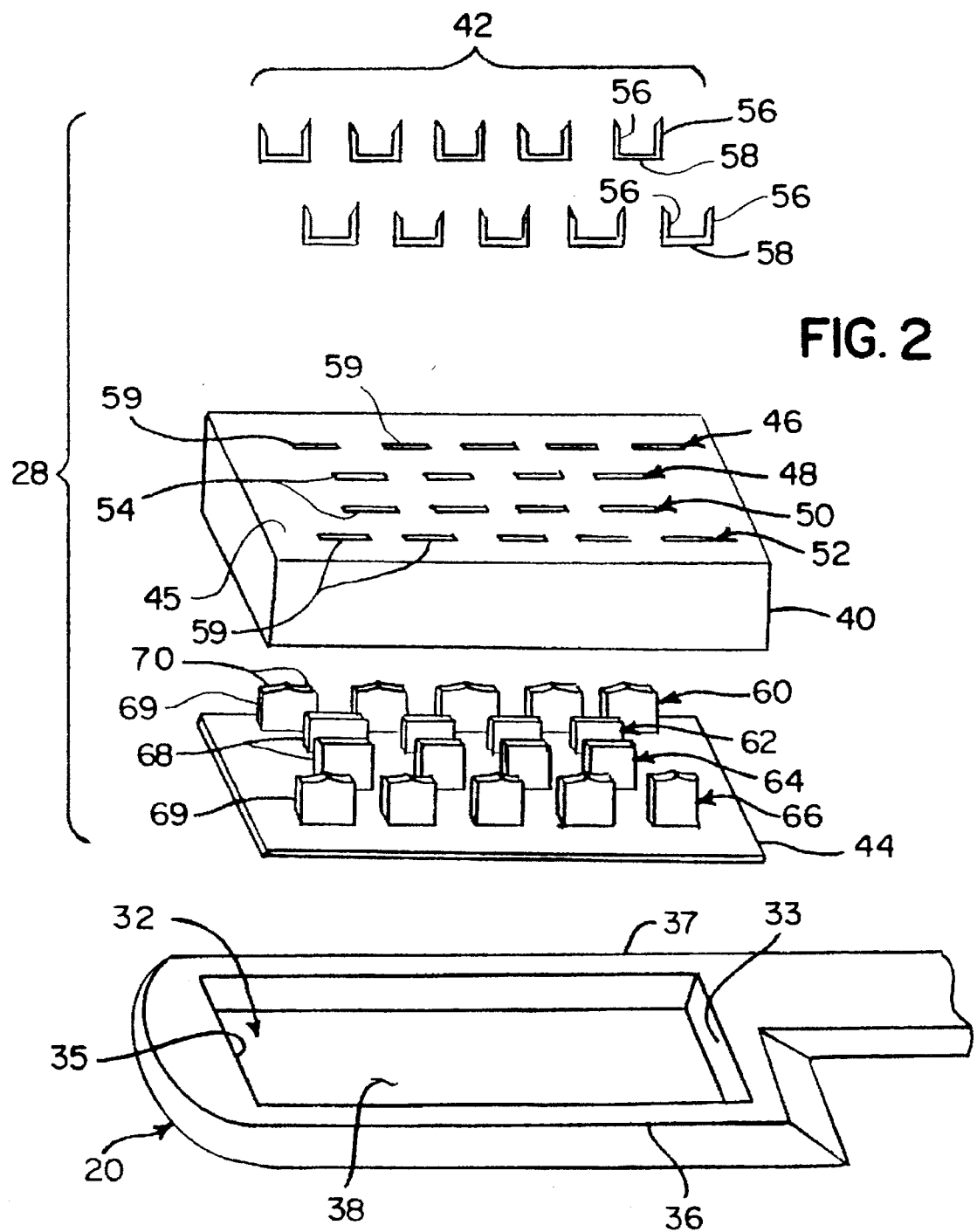
FIG. 2 is an exploded perspective view of a first jaw and staple cartridge of the surgical stapler of FIG. 1.
Figure 4:
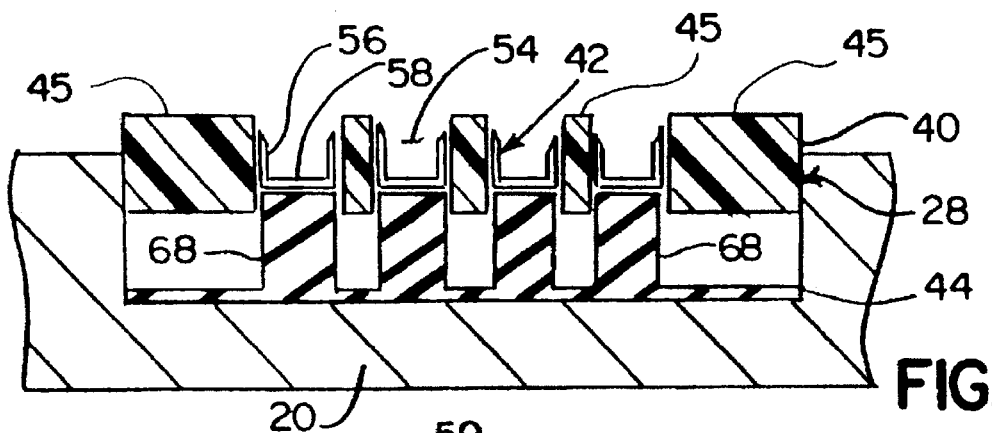
FIG. 4 is a cross-sectional view of the staple cartridge of FIG. 3 taken through line 4—4.
Figure 5:
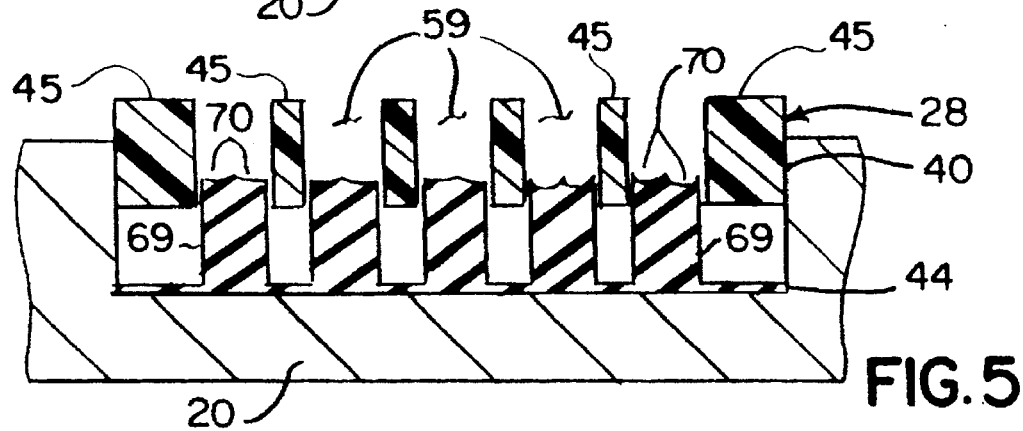
FIG. 5 is a cross-sectional view of the staple cartridge of FIG. 3 taken through line 5—5.
Figure 3:
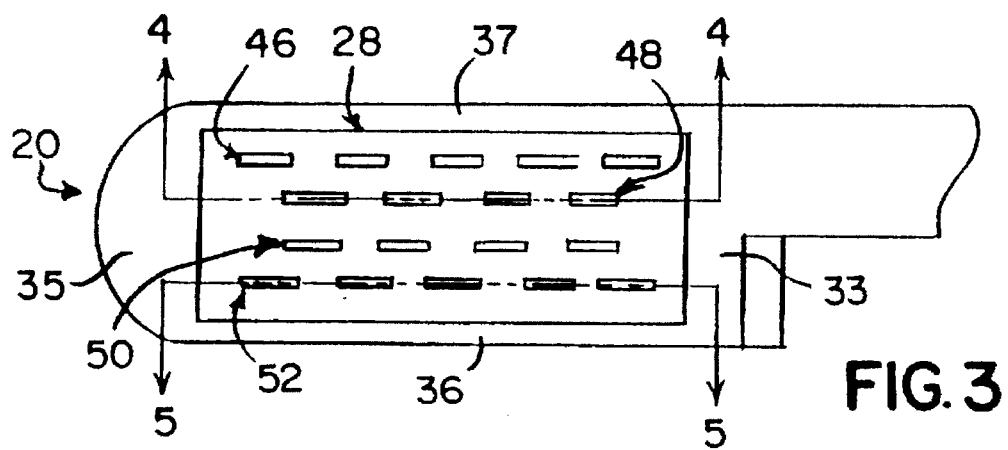
FIG. 3 is a top view of an assembled staple cartridge supported in the first jaw of the surgical stapler.

As best seen in FIG. 2, the first jaw 20 includes a cavity 32 therein, defined by spaced, opposing side walls 36 and 37, spaced, opposing end walls 33 and 35, and a back wall 38. Cavity 32 is configured to hold staple cartridge 28, which is formed of a body 40, a plurality of surgical staples 42 and a base plate 44. Cartridge body 40 and base plate 44 are generally rectangular and are frictionally held along respective peripheral edges thereof in vertically spaced relation within cavity 32 as shown in FIGS. 3–5. A tissue engaging surface 45 of cartridge body 40 protrudes from jaw 20 into the tissue receiving space between the first and second jaws 20 and 22, and has spaced parallel rows 46, 48, 50 and 52 of spaced openings or slots extending therethrough.

Inner rows 48 and 50 are made up of staple slots 54 which are configured to support and guide staples 42 carried therein. Staples 42 are preferably conventional metal surgical staples of the type presently used in mass stapling instruments and having a pair of deformable tissue penetrating legs 56 connected by a cross-member or web 58. The tissue penetrating legs 56 of staples 42 extend upwardly within staple slots 54 towards the tissue engaging surface 45 as shown in FIG. 4. Outer rows 46 and 52 are made up of anvil slots 59, which do not carry staples, as shown in FIG. 5.

Cartridge base plate 44 has spaced parallel rows 60, 62, 64 and 66 of protrusions which are aligned with and extend into rows 46, 48, 50 and 52 of staple and anvil slots defined in cartridge body 40. Inner rows 62 and 64 of the base plate protrusions are made up of staple drivers 68 configured to engage the webs 58 of staples 42 and to be received snugly within staple slots 54 of cartridge body rows 48 and 50. Similarly, outer rows 60 and 66 of the base plate protrusions are made up of anvils 69 configured to be snugly received into anvil slots 59 of cartridge body rows 46 and 52. Anvils 69 each have a pair of arcuate indentations 70 formed on an upper surface facing staples 42 in the second jaw 22 to receive, bend inward and crimp the tissue engaging legs 56 of these surgical staples 42 when the staples 42 are urged into indentations 70.

Figure 6:
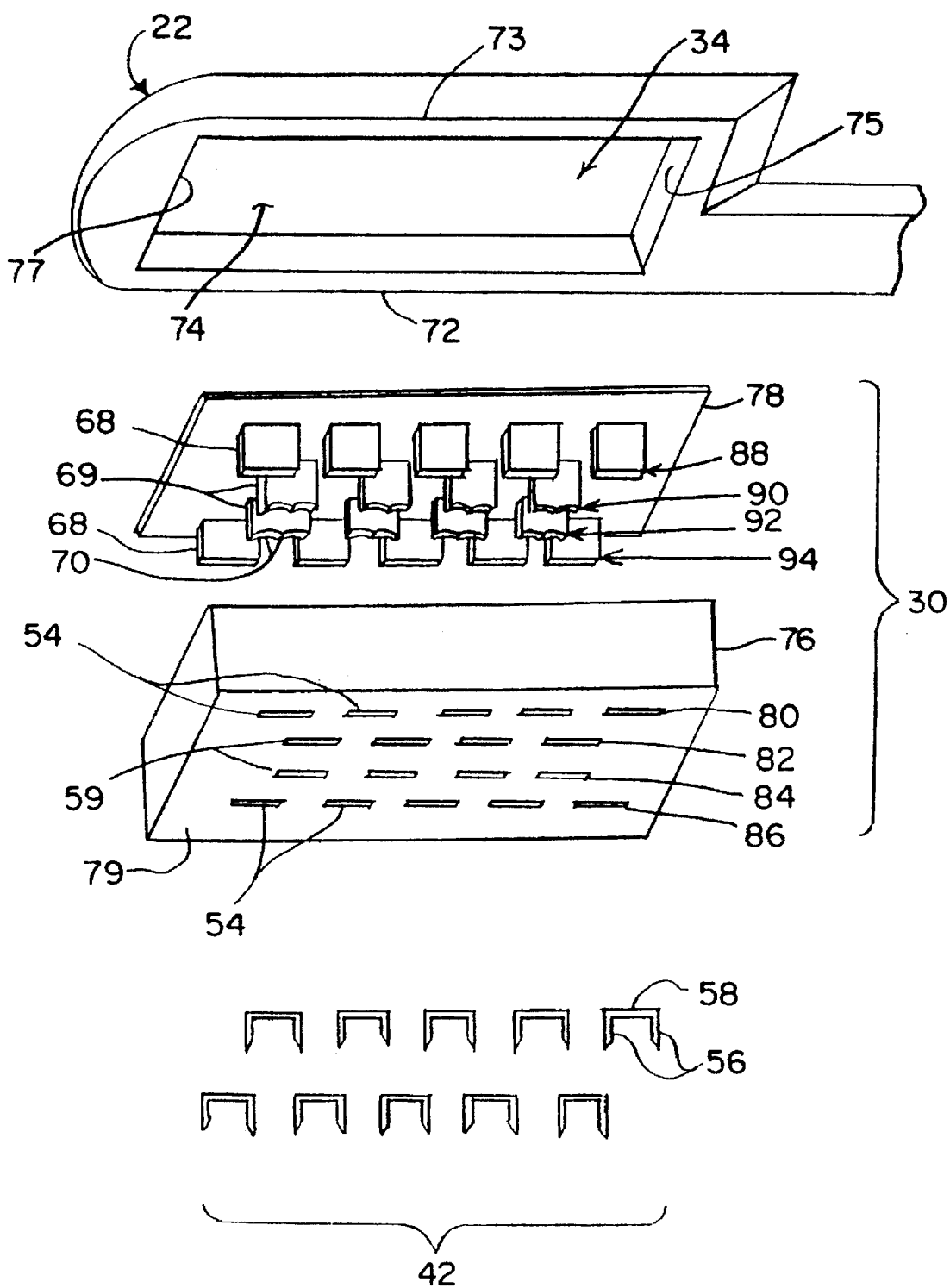
FIG. 6 is an exploded perspective view of a second jaw and staple cartridge of the surgical stapler of FIG. 1.
Figure 8:
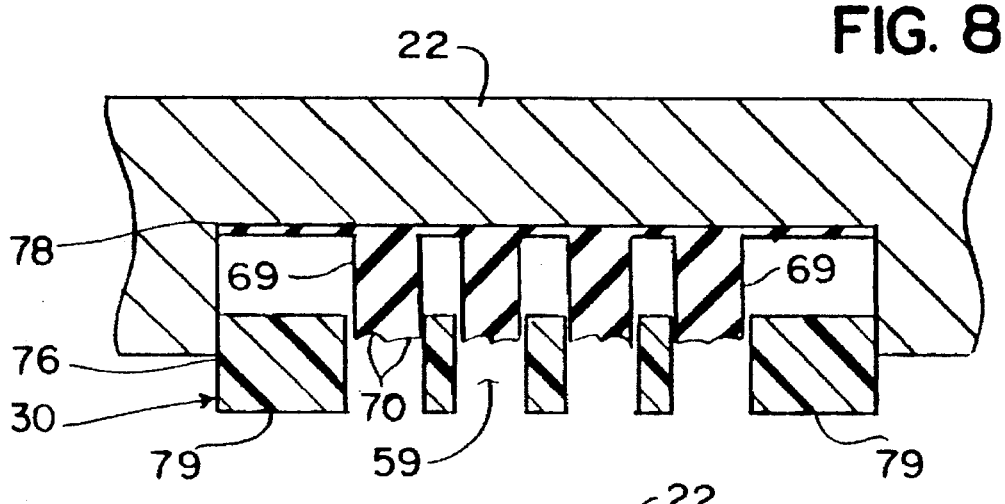
FIG. 8 is a cross-sectional view of the staple cartridge of FIG. 7 taken through line 8—8.
Figure 9:
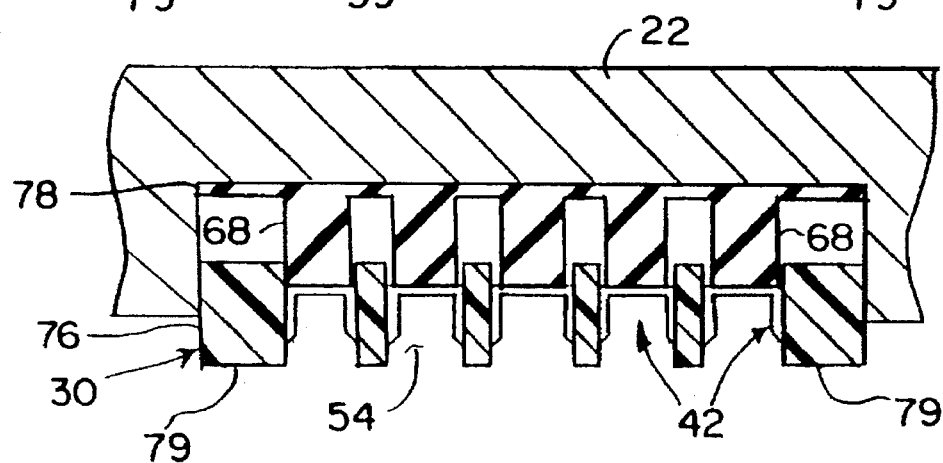
FIG. 9 is a cross-sectional view of the staple cartridge of FIG. 7 taken through line 9—9.
Figure 7:
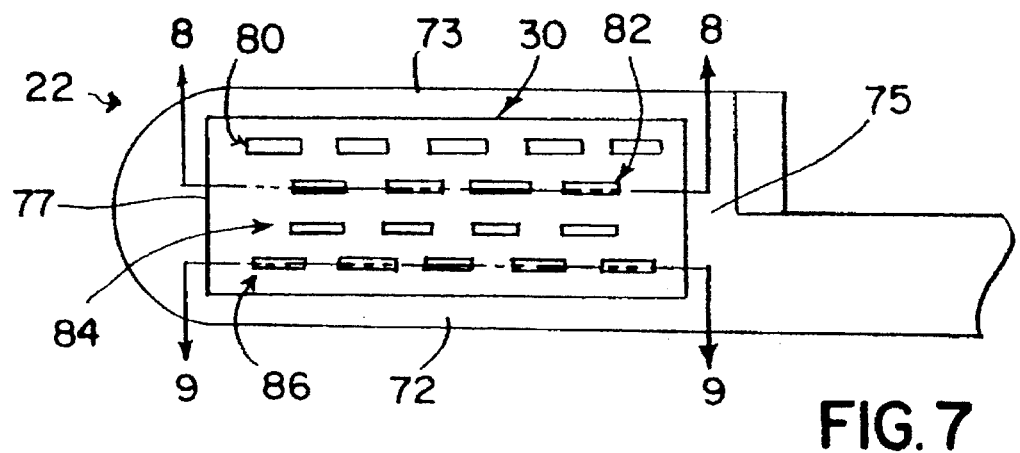
FIG. 7 is a bottom view of an assembled staple cartridge supported in the second jaw of the surgical stapler.

As shown in FIG. 6, the second jaw 22 has a cavity 34 therein, defined by spaced, opposing side walls 72 and 73, spaced, opposing end walls 75 and 77 and a back wall 74. Cavity 34 is configured to hold staple cartridge 30, which is formed of a body 76, a plurality of surgical staples 42 and a base plate 78. Cartridge body 76 and base plate 78 are generally rectangular and are frictionally held along respective peripheral edges thereof in vertically spaced relation within cavity 34 as shown in FIGS. 7–9. A tissue engaging surface 79 of cartridge body 76 protrudes from jaw 22 into the tissue receiving space between the first and second jaws. 20 and 22, and has spaced parallel rows 80, 82, 84 and 86 of spaced slots extending therethrough. Outer rows 80 and 86 are made up of staple slots 54 configured to support and guide staples 42 carried therein as shown in FIG. 9. Inner rows 82 and 84 are made up of anvil slots 59 which do not carry staples, as shown in FIG. 8. Base plate 78 of staple cartridge 30 has spaced parallel rows 88, 90, 92 and 94 of protrusions which are aligned with and extend into spaced parallel rows 80, 82, 84 and 86 of spaced slots in cartridge body 76. Inner rows 90 and 92 of spaced protrusions are anvils 69 with arcuate indentations 70 for receiving, bending and crimping tissue penetrating legs 56 of staples 42 held in jaw 20. Anvils 69 are aligned with anvil slots 59 in cartridge body 76. Outer rows 88 and 94 of spaced protrusions on base plate 78 are staple drivers 68 which are configured to engage the webs 58 of staples 42 held in staple slots 54 of cartridge body 76.

Figure 10:
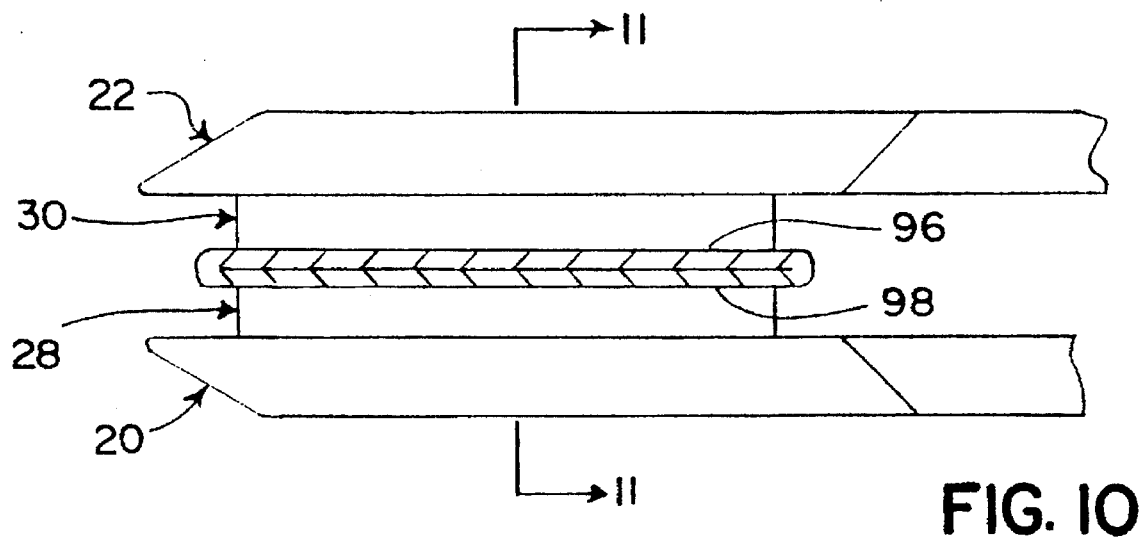
FIG. 10 is a side view of a distal portion of the surgical stapler clamping biological tissue between opposed jaws and staple cartridges.

A side view of the distal portion of the surgical stapler 10 according to the present invention is shown in FIG. 10. In this view, a tubular vessel of biological tissue is compressed between staple cartridges 28 and 30 held by first and second jaws 20 and 22, respectively. An upper wall 96 of the compressed tubular vessel contacts staple cartridge 30 held in the first jaw 20, while a lower wall 98 of the tubular vessel contacts staple cartridge 28 held by the second jaw 22. Staple cartridges 28 and 30 are thus disposed on opposite sides of the compressed tubular vessel.

Figure 11:
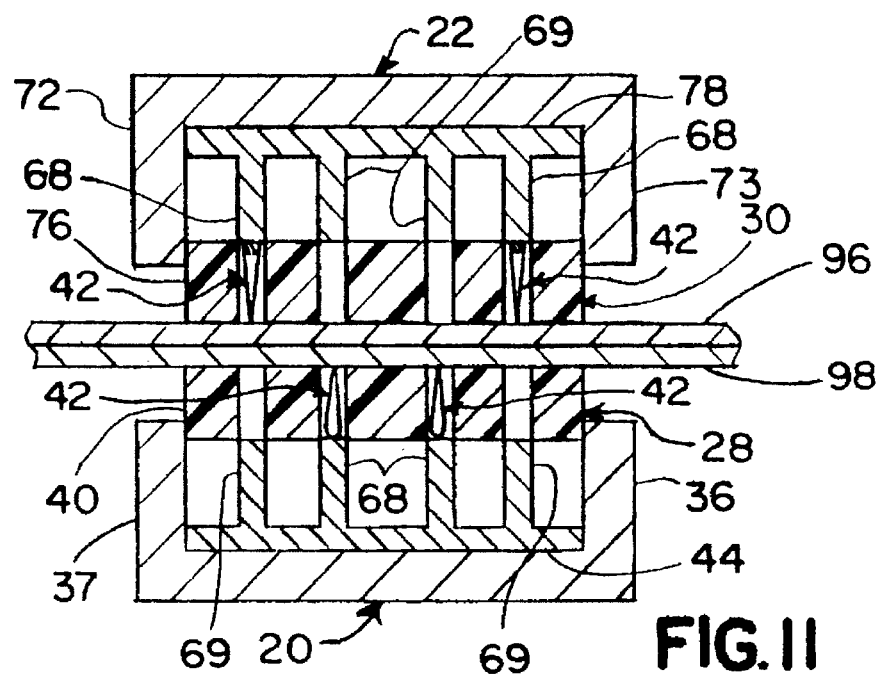
FIG. 11 is a cross-sectional view of opposed jaws and staple cartridges taken through line 11—11 in FIG. 10.

FIG. 11 is a sectional view, taken through line 11—11 in FIG. 10 to illustrate how the various features of staple cartridges 28 and 30 align when first and second jaws 20 and 22 are clamped against tissue layers 96 and 98. More particularly, when the jaws 22 and 20 are held in opposed relation as shown, anvils 69 in the first staple cartridge 28 align with staple drivers 68 in the second staple cartridge 30. Similarly, anvils 69 in the second cartridge 30 align with staple drivers 68 in the first staple cartridge 28. Outer rows of staples 42 are held in cartridge body 76 with tissue piercing legs 56 facing tissue wall 96 while inner rows of staples 42 are held in cartridge body 40 with tissue piercing legs 56 facing tissue wall 98. This arrangement results in outermost and innermost rows of staples being applied respectively from opposite sides of the body tissue.

Figure 12:
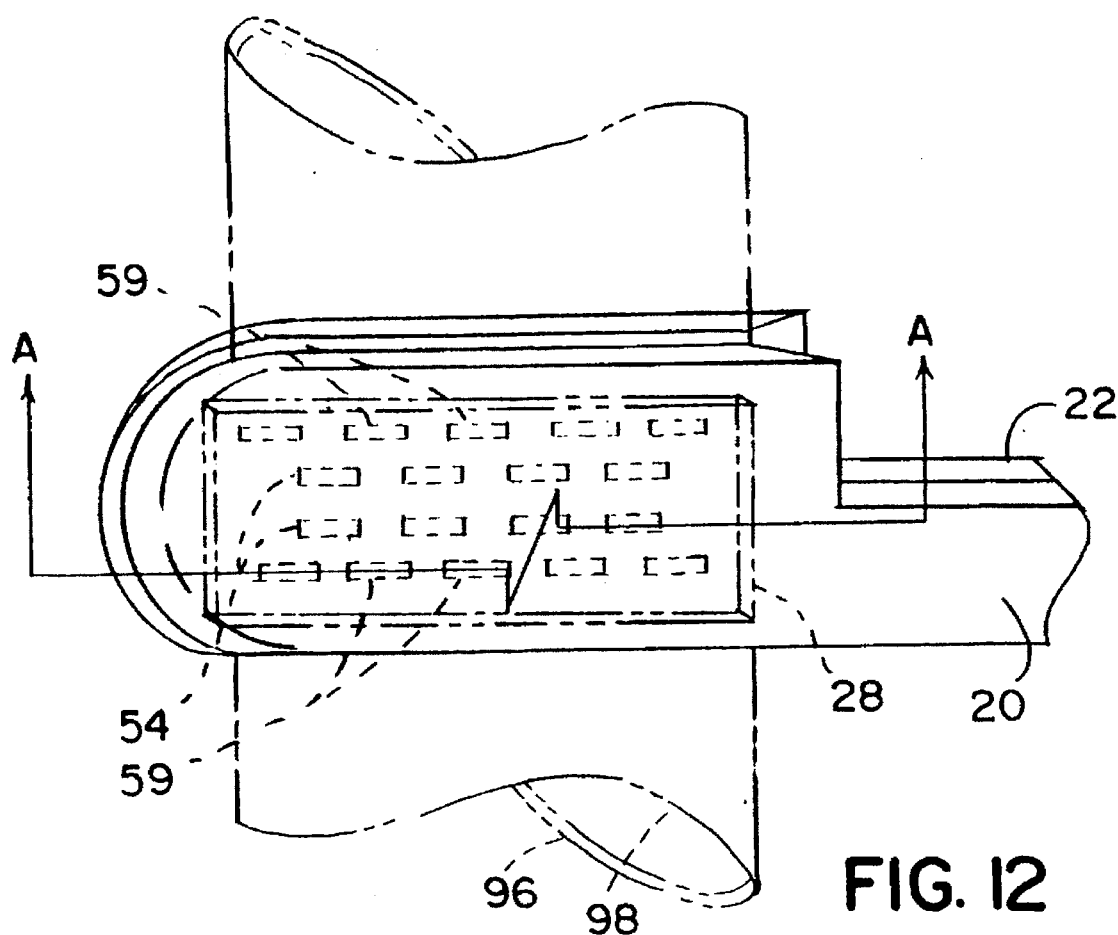
FIG. 12 is a bottom view of a distal portion of the surgical stapler clamping biological tissue between opposed jaws and staple cartridges.

Use of the surgical stapler 10 of the present invention will be described with reference to FIG. 12 which is a bottom view of the distal portion of the stapler clamped around tissue to be ligated. Cartridge 28 is indicated with broken lines in this Figure, as are the staple and anvil slots 54 and 59 formed therein. FIGS. 13–17 are broken sectional views taken along line 13—13 in FIG. 12 through adjacent rows of staples and anvils to show the staples being applied from both sides of the tissue being joined. Thus, left and right sides of each Figure represent separate rows of staples and anvils.

In use, the first staple cartridge 28 with staples 42 disposed upwardly in each staple slot 54 and staple drivers 68 and anvils 69 of base plate 44 slidably received into cartridge staple slots 54 and anvil slots 59, respectively, is inserted into cavity 32 of jaw 20 of surgical stapler 10. The second staple cartridge 30, with staples disposed downwardly in each staple slot 54 and staple drivers 68 and anvils 69 of base plate 78 slidably received into cartridge staple slots 54 and anvil slots 59, respectively, is inserted into cavity 34 of jaw 22 in the same way. Using handles 16 and 18 (FIG. 1) to manipulate the instrument as one would use a conventional clamp or forceps, tissue layers 96 and 98 to be fastened are positioned between jaws 20 and 22 as shown in FIG. 13. Handles 16 and 18 are pressed toward one another to cause pivoting, or closing of jaws 20 and 22 and cartridges 28 and 30 towards one another and thus towards the tissue received between jaws 20 and 22 and cartridges 28 and 30. With cartridges 28 and 30 compressed against opposite sides of the tissue 96 and 98 as shown in FIG. 14, further clamping of the jaws 20 and 22 causes the cartridge bodies 40 and 76 to slide or sink into cavities 32 and 34, respectively, advancing staple drivers 68 and anvils 69 in each jaw through the staple slots 54 and anvil slots 59 in the receding cartridge bodies 40 and 76 toward the layers of tissue 96 and 98. Continued compression of jaws 20 and 22 against tissue layers 96 and 98 pushes staple drivers 68 and anvils 69 in both jaws toward each other forcing the legs 56 of staples 42 held therebetween through the tissue from both sides, as shown in FIG. 15, and towards arcuate indentations 70 on the approaching opposed anvils 69, where the legs 56 are bent inwardly into a clinched tissue-holding configuration on both sides of the tissue being joined.

Compression of jaws 20 and 22 and bending of staple legs 56 continues until the gap spacer 26 extending from leg 12 seats on leg 14 (see FIG. 1), at which point the stapling process is complete and the tissue is fastened by staples applied from both directions. At this point, pressure on handles 16 and 18 is relaxed to allow leaf spring 25 to urge the handles apart and to rotate jaws 20 and 22 apart and away from the joined tissue as shown in FIG. 17. Webs 58 and crimped tissue-penetrating legs 56 of surgical staples 42 on a given side of the tissue being joined are staggered longitudinally when applied, as shown in FIG. 18, so that the crimped tissue penetrating legs 56 are aligned with interstices between webs 58 in an adjacent row of staples helping to assure effective hemostasis along rows of finished staples.

It will also be appreciated that webs 58 and crimped tissue-penetrating legs 56 of surgical staples 42 on a given side of the tissue being joined can be placed in longitudinal alignment with each other, as shown in FIG. 19. Aligning the staples in such a manner allows an equal number of staples to be placed in adjacent coextensive rows.

After the staples have been applied, the surgical stapler can be withdrawn from the site or a knife blade assembly of conventional design can be actuated to perform a cutting procedure between adjacent parallel rows of staples (e.g., along lines B—B and C—C in FIGS. 18 and 19). The depth of the gap can be adjusted to accommodate various thicknesses of tissue encountered in different procedures by altering the heights of the staple drivers and anvils or the height of the gap spacer 26.

By applying surgical staples from both sides of tissue to be fastened a much more complete and permanent ligation can be effected. Each side of the stapled tissue will have both webs and clinched tissue-penetrating legs of surgical staples applying holding pressure to the sutured area, equalizing and distributing the fastening pressures more evenly through the tissue to better control hemostasis.

A modification of the surgical stapler of the present invention, for use in laparoscopic or endoscopic procedures where the surgery is performed through a small incision or sleeve, is shown in FIG. 20. The stapler 110 includes an elongate body 112 for insertion through the incision or sleeve, a pair of legs 114 and 116 angled sharply down from a proximal end of the elongate body 112 and having loop handles 118 and 120 at respective proximal ends thereof, and a pair of opposed jaws 122 and 124 extending from a distal end of the elongate body 112. Jaws 122 and 124 are essentially the same as jaws 20 and 22 previously described, with the exception that jaw 122 is fixed to elongate body 112 and jaw 124 is rotatable about a pivot 126 on elongate body 112 in opposable relation to jaw 122. Staple cartridges 128 and 130 are held by jaws 122 and 124, respectively, and are essentially the same as cartridges 28 and 30 previously described.

Leg 116 of the surgical stapler 110 is fixed at a nearly perpendicular angle to the proximal end of elongate body 112 and carries a fulcrum pin 132 on a back face about which leg 114 is rotatable to cause pivoting of rotatable jaw 124 using conventional force transmission techniques. A gap spacer 134 extends from fixed leg 116 toward rotatable leg 114 to establish a minimum gap therebetween while a leafspring 136 normally urges the legs 114 and 116 apart.

In use, a small incision is made through the wall of an anatomical cavity with a penetrating instrument, such as a trocar, and, if a sleeve is to be used, the sleeve is inserted over the penetrating instrument into the cavity wall. The penetrating instrument is then removed, leaving either the incision itself or the sleeve for use as a portal for introduction of the stapler 110 into the anatomical cavity. Prior to insertion, the surgical stapler 110 is grasped by placing a thumb through the proximal loop handle 118 and one or more fingers through the distal loop handle 120. The loop handles 118 and 120 are manipulated to pivot leg 114 toward leg 116 around fulcrum pin 132 to place the pivoted jaw 124 in opposed, spaced relation to fixed jaw 122 as shown in FIG. 21 so that staple cartridges 128 and 130 are held closely together without contacting. With jaws 122 and 124 held in closely spaced relation, the distal end of the elongate body 112 is inserted through the incision or sleeve into the anatomical cavity. Once inside the anatomical cavity, leg 118 of the stapler is allowed to pivot away from leg 116 under the influence of leaf spring 136 to separate the jaws 122 and 124 as shown in FIG. 20. Biological tissue 138 to be ligated is then positioned within the tissue receiving space between the jaws 122 and 124 and staple cartridges 128 and 130 held therein. With the biological tissue 138 positioned between jaws 122 and 124, leg 114 is once again pivoted toward leg 116 using loop handles 118 and 120 externally of the anatomical cavity, until leg 114 bears against gap spacer 134 which extends from leg 116. Rotation of leg 114 toward leg 116 causes pivoted jaw 124 to rotate around pivot 126 in the direction of fixed jaw 122. Cartridges 128 and 130 held by jaws 122 and 124, respectively, are compressed against the biological tissue on opposite sides thereof so that their respective staple cartridge bodies will recede into cavities formed in jaws 122 and 124 as shown in FIG. 22, allowing staple drivers and anvils in each jaw to advance through openings defined in the cartridge bodies to drive and crimp the tissue penetrating legs of staples applied from both sides of the tissue. A cut can then be made between finished rows of staples using conventional techniques, and/or the stapler withdrawn from the cavity for disposal or sterilization and reuse.

A further modification of the surgical stapler of the present invention is shown in FIGS. 23 and 24 wherein the primary difference is the mechanism for driving the staples from one jaw into the other. The surgical stapler 210 includes a pair of spaced parallel jaws 212 and 214 connected at proximal ends thereof to a handle 216 and configured to receive staple cartridges 218 and 220, respectively. A blade 222 is suspended between the spaced parallel jaws 212 and 214 and is movable within grooves 224 formed longitudinally along the length of each staple cartridge 218 and 220. As best seen in FIG. 24, a plurality of spaced rows of staple slots 226 and staple-forming anvils 227 are formed in tissue engaging surfaces of the cartridges 218 and 220 on both sides of the grooves 224 and are longitudinally staggered in the manner previously described.

The handle 216 is suitably shaped to form a hand grip to facilitate the handling and operation of the stapling instrument and includes an actuator knob 228 which extends through and slides within an elongated slot 230 formed in one side of the handle 216. A latching mechanism including a latch arm 232 is pivotably connected to the housing 216 for latching the jaws 212 and 214 together at an intermediate position along the length of the jaws. The handle 216, actuator knob 228, and latch arm 232 resemble other conventional surgical stapling instruments, such as that described in U.S. Pat. No. 4,633,874 to Chow, et al., which is incorporated herein by reference.

Figure 25:
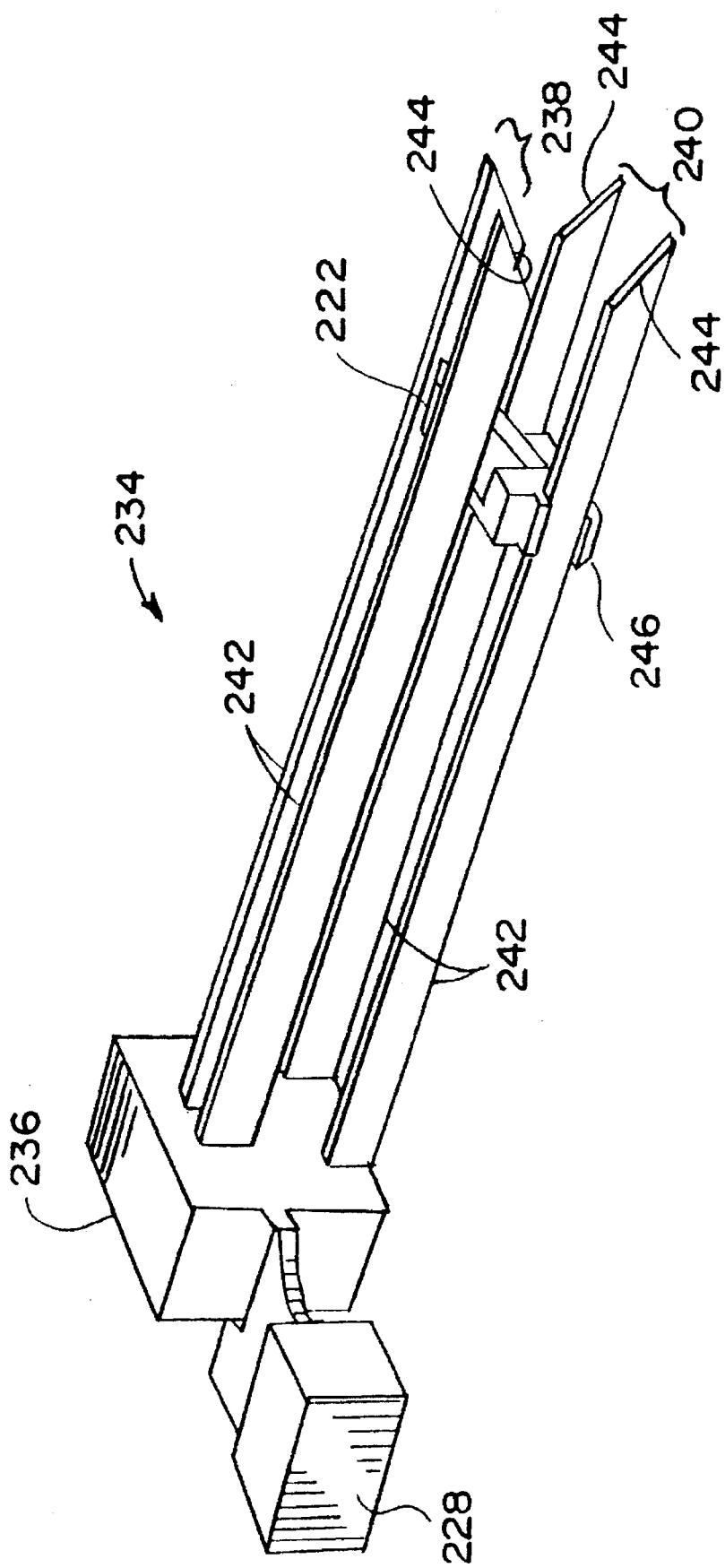
FIG. 25 is a perspective view of a pusher bar and knife blade assembly for use in the surgical stapler of FIG. 23.

The surgical stapler 210 further includes a pusher bar and knife blade assembly 234, shown in FIG. 25, which is slidably mounted within handle 216 for longitudinal movement relative to the spaced parallel jaws 212 and 214, respectively, for driving staples from staple cartridges 218 and 220 into tissue gripped between the jaws, forming the staples against anvils held in each jaw, and cutting the tissue along a line between the rows of staples formed in the tissue. The pusher bar and knife blade assembly 234 includes a pusher block 236 for being slidably disposed within the handle 216 and connected with the actuator knob 228. Two pairs 238 and 240 of spaced, parallel pusher bars 242 project forward from the pusher block 236 and have wedge-shaped tips 244 at distal ends thereof which define inclined cam surfaces for engaging staple drivers in staple cartridges 218 and 220. The spacing between pusher bars 242 of a given pair 238 or 240 corresponds to the spacing between staple slots 226 in cartridges 218 and 220, respectively, and is thus different for each pair. A knife block 246 is supported between one pair 240 of pusher bars 242 to carry an inclined knife blade 222 having a forward-facing beveled cutting edge. The knife blade 222 extends between both pairs 238 and 240 of pusher bars 242 and is positioned proximally of the wedge-shaped tips 244.

Figure 26:
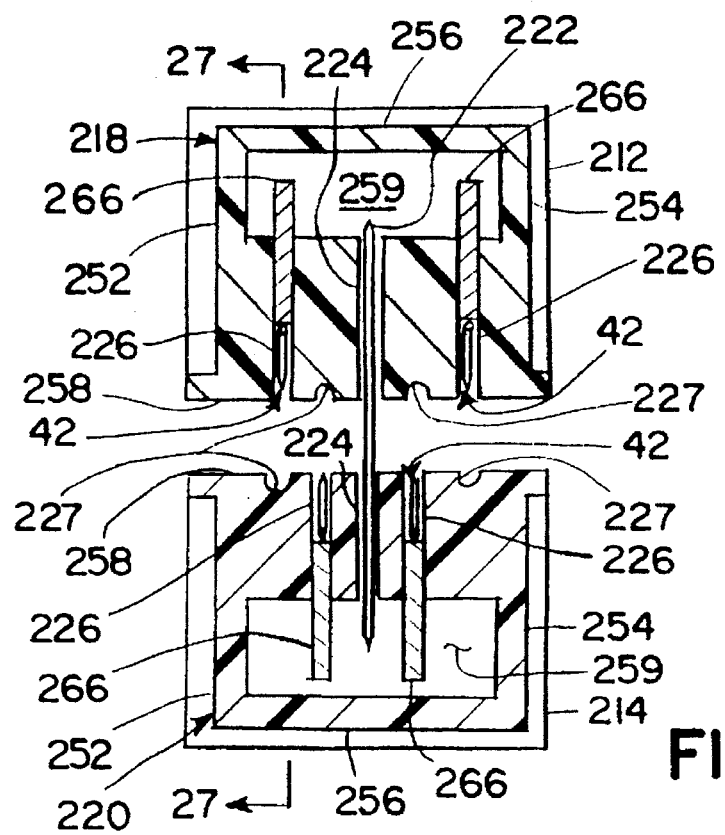
FIG. 26 is a cross-sectional view of the stapler of FIG. 23 taken along line 26—26.
Figure 27:
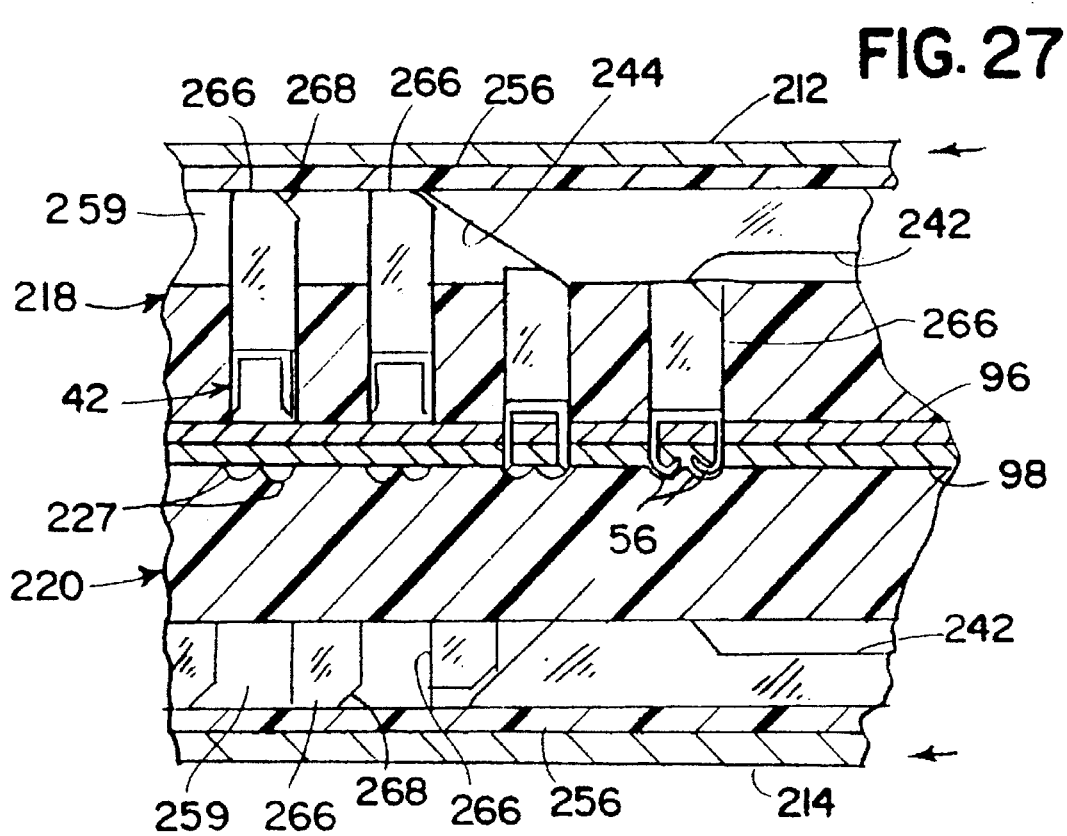
FIG. 27 is a cross-sectional view taken along line 27—27 in FIG. 26.

As shown in FIGS. 26 and 27, jaws 212 and 214 are configured to receive staple cartridges 218 and 220, respectively. Each of the cartridges 218 and 220 is a generally rectangular, and includes a pair of spaced, opposing side walls 252 and 254, a back wall 256 connected between the side walls 252 and 254 and a tissue engaging wall 258 spaced above the back wall 256 and also connected between the side walls 252 and 254. Together, the spaced, opposed side walls 252 and 254, back wall 256 and tissue engaging wall 258 of each cartridge define an elongated cavity 259 therebetween for receiving a pair of pusher bars 242. In addition, a continuous longitudinal groove 224 is defined along the length of the tissue engaging wall 258 to guide the knife blade 222, and at least two parallel rows of longitudinally spaced staple slots 226 are defined on opposite sides of the groove 224 to support and guide staples 42 carried therein. Staple drivers 266 are rectangular bars frictionally held within the staple slots 226 behind the staples 42 and protruding from staple slots 226 into the elongated cavity 259. As best seen in FIG. 27, each staple driver 266 has on its protruding end a slanted surface 268 oriented at a similar angle to the cam surface formed by wedge-shaped tips 244 of each pusher bar 242 to provide a flat, sliding contact between the surfaces. A pair of parallel rows of longitudinally spaced staple-forming anvils or indents 227 are also formed in the tissue engaging wall 258 of each cartridge on opposite sides of the groove 224.

In the first cartridge 218, the staple slots 226 in the tissue engaging wall 258 which carry the staples 42 are spaced laterally outward from the staple-forming anvils 227. Conversely, in the second staple cartridge 220, the staple slots 226 in the tissue engaging wall 258 which carry the staples 42 are located laterally inward of the staple-forming anvils 227 formed in the tissue engaging wall 258. Thus, the staples 42 carried by the first cartridge 218 are aligned with staple-forming anvils 227 in the second cartridge 220 and the staples 42 in the second cartridge 220 are aligned with staple-forming anvils 227 in the first cartridge 218, respectively. As described previously in connection with surgical stapler 10, inner and outer rows of staples are arranged so that their webs are longitudinally staggered on opposite sides of the tissue to be joined.

In use, the staple cartridges 218 and 220 are loaded into the first and second spaced parallel jaws 212 and 214 with the pusher bars 242 and knife blade 222 retracted into the handle 216. The biological tissue 96 and 98 to be ligated is then positioned between the first and second jaws 212 and 214 and staple cartridges 218 and 220 and held in place by actuation of a latching mechanism which places the jaws 212 and 214 at an intermediate position whereby the tissue 96 and 98 is clamped between the two jaws. After the tissue is clamped between the two jaws, the surgical stapler 210 is fired by advancing the actuator knob 228 distally to translate the pusher bar and knife blade assembly 234. During the initial advance of the pusher block 246, the pusher bars 242 slide through the elongated cavity 259 defined in each staple cartridge placing the wedge-shaped tips 244 of the pusher bars 242 into engagement with the slanted surfaces 268 of the staple drivers 266 to sequentially drive the staple drivers 266 into the staple slots 226 and thus the staples 42 from the staple cartridges 218 and 220 through the tissue, and to form the tissue penetrating legs 56 against the staple-forming anvils 227 on both sides of the tissue. At the same time, the knife block 246 advances to move the knife blade 222 in tandem with the pusher bars 242 through the central longitudinal groove 224 between the rows of finished or formed staples to cut the tissue gripped between the jaws 212 and 214. After the pusher block 236 is fully advanced to form all of the staples in the cartridges, the pusher block 236 is retracted toward its start position by retraction of the actuator knob 228. The jaws 212 and 214 are then released in a conventional manner by operation of the latching mechanism and the stapler removed from the operative site for disposal or sterilization and reuse.

Figure 28:
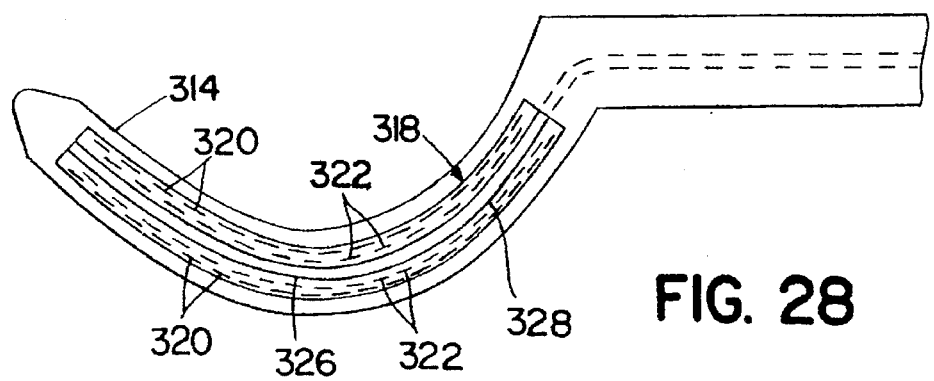
FIG. 28 is a top view of a curved jaw for use in the surgical stapler of the present invention.
Figure 29:
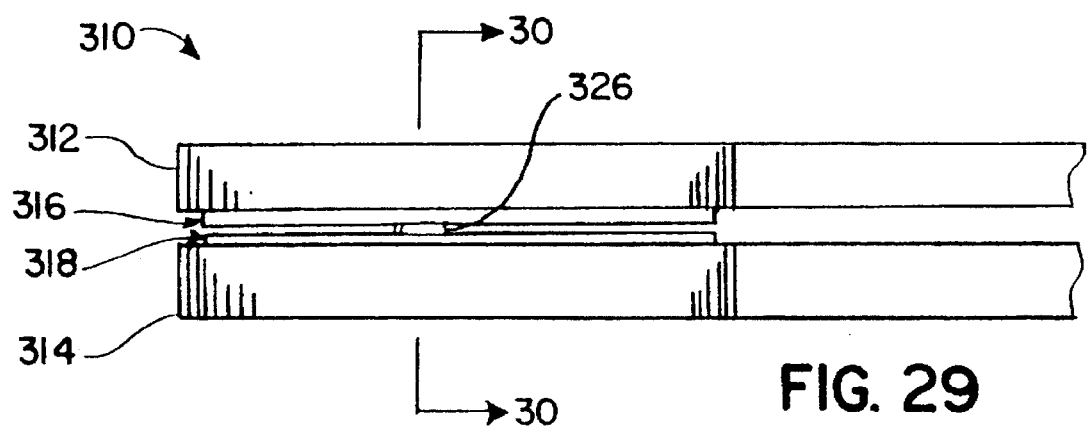
FIG. 29 is a side view of curved jaws in opposed relation.
Figure 30:
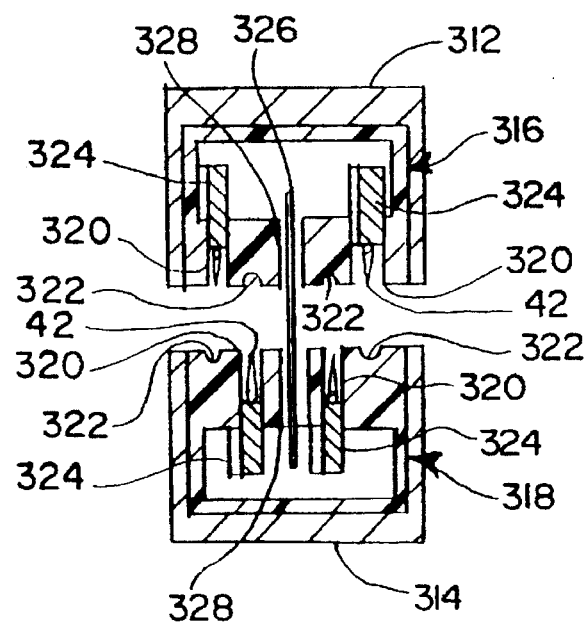
FIG. 30 is a cross-sectional view of the curved jaws taken along line 30—30 in FIG. 29.

In a further modification, shown in FIGS. 28–30, the surgical stapler 310 includes spaced, parallel jaws 312 and 314 which are curved to apply arcuate rows of staples thereby providing improved access in certain procedures and facilitating severing of vessels closer to the organ in order to minimize the amount of tissue suspended therefrom. The jaws 312 and 314 are essentially the same as jaws 212 and 214 previously described with the exception of their curved shape and the corresponding curved shape of the staple cartridges 316 and 318 held therein. Thus, the staples 42 held in staple slots 320 and the anvils 322 formed in the opposed cartridges are arranged so that the inner rows of staples 42 are placed from one side of the biological tissue fastened and the outer row of staples 42 are placed from the other side. A cam mechanism (not shown), similar to that previously described, advances pusher bars through the first and second cartridges 316 and 318 using conventional force transmission techniques to force staple drivers 324 into staple slots 320 to drive staples 42 through the tissue to be joined and into anvils 322. Additionally, a very narrow knife or wire 326 is carried behind the cam surface of the pusher bars within curved grooves 328 formed along the length of each cartridge 316 and 318 to cut between rows of finished staples. Only the distal portions of the surgical stapler 310 have been illustrated in FIGS. 28 and 29; however, it will be appreciated that the proximal portions can be formed with any cooperating structure.

Figure 31:
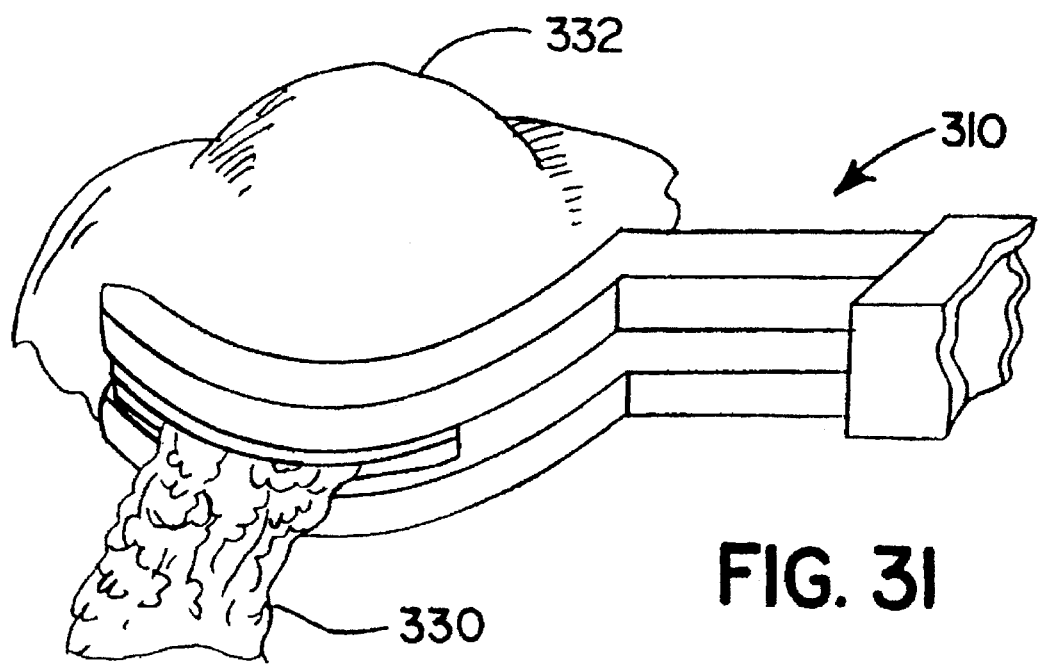
FIGS. 31–32 are perspective views illustrating use of the curved jaws to apply rows of staples to vessels surrounding a curved organ.
Figure 32:
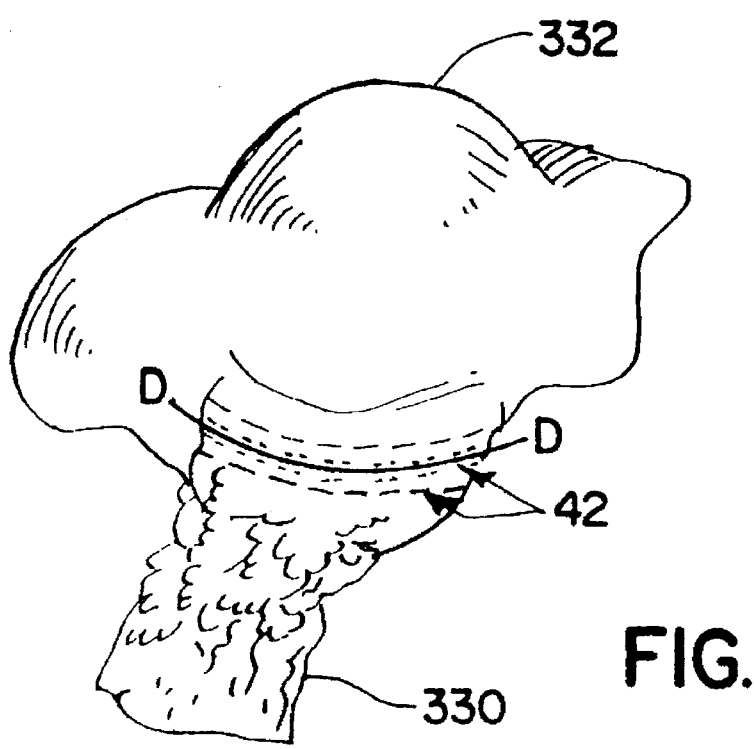

FIGS. 31 and 32 illustrate an exemplary use of the surgical stapler 310. In FIG. 31, curved jaws 312 and 314 of the stapler 310 are shown clamped against vessels 330 leading from a curved organ 332, such as the hilus. The curved profile of the jaws 312 and 314 allows the stapler 310 to be positioned close to the organ 332 and to apply rows of staples into the vessels 330 in a pattern conforming approximately to an exterior curvature of the organ 332. As the staples are fired sequentially by advancement of an actuator knob or the like, the knife blade or wire 326 moves in tandem to cut between the stapled vessels clamped between the jaws along the line D—D shown in FIG. 32. The actuator knob is then retracted and the jaws released in the manner previously described in connection with surgical stapler 210.

Another modification of the surgical stapler of the present invention is shown in FIGS. 33–36, wherein a surgical stapler 410 is similar to surgical stapler 110 and has hinged cartridges and an integral knife blade assembly. For purposes of illustration, only the distal portions of the surgical stapler 410 have been illustrated in FIGS. 33–36; however, it will be appreciated that the proximal portions can be formed with any cooperating structure, such as that shown in FIG. 20.

The surgical stapler 410 includes a pair of staple cartridges 412 and 414 having rectangular cartridge bodies 416 and 418 connected at proximal ends thereof by a living hinge 419 formed of the same material as the cartridge bodies 416 and 418, which is preferably a plastic. The opposed cartridge bodies 416 and 418 are frictionally held within rectangular cavities 420 and 422 formed on opposed faces of stapler jaws 424 and 426. Base plates 428 and 430, each carrying staple drivers 432 and anvils 434, are frictionally held at the bottom of cavities 420 and 422 and are vertically spaced from cartridge bodies 416 and 418 with staple drivers 432 and anvils 434 penetrating into cartridge bodies 416 and 418 through a plurality of staple and anvil chambers 436 and 437 extending between respective tissue engaging faces 438 and 439 and back faces 440 and 441 of cartridge bodies 416 and 418. Staples 442 are the same as staples 42 in surgical stapler 110 and are carried in staple chambers 436 ahead of staple drivers 432. The arrangement of staples 442 and staple forming anvils 434 in each of the cartridges 412 and 414 is the same as the arrangement previously described in connection with surgical stapler 10, with staples in each cartridge being aligned with anvils in the other cartridge.

A knife blade 444 is suspended between knife blocks 446 and 448 slidably disposed in elongated rectangular grooves 450 and 452 formed on back faces 440 and 441 of cartridge bodies 416 and 418. A pair of continuous narrow slits 454 and 456 extend between grooves 450 and 452 and tissue engaging faces 438 and 439, respectively to provide an opening through which the knife blade 444 can extend. Additionally, slotted openings 458 and 460 are formed through the bottoms of cavities 420 and 422 in jaws 424 and 426 in alignment with the elongated rectangular grooves 450 and 452 formed on the back faces 440 and 441 of cartridge bodies 416 and 418.

Figure 33:
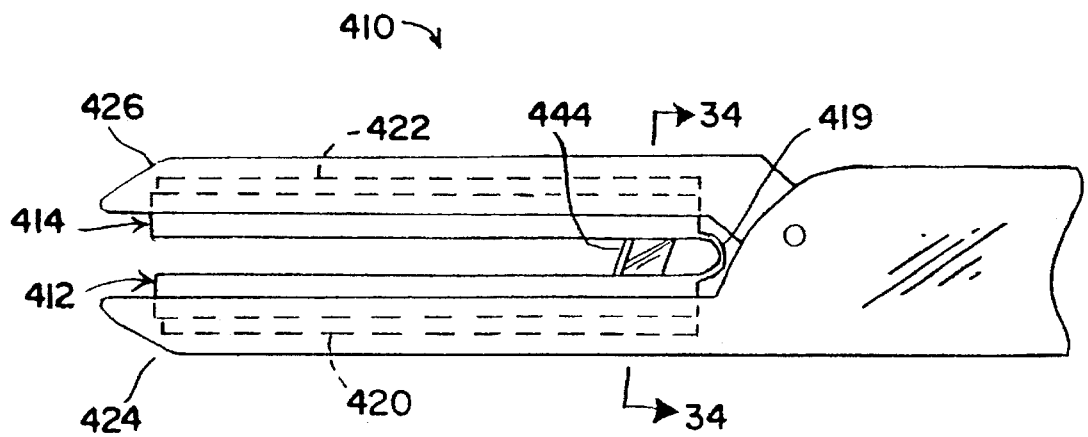
FIG. 33 is a side view of a modified surgical stapler according to the present invention.
Figure 34:
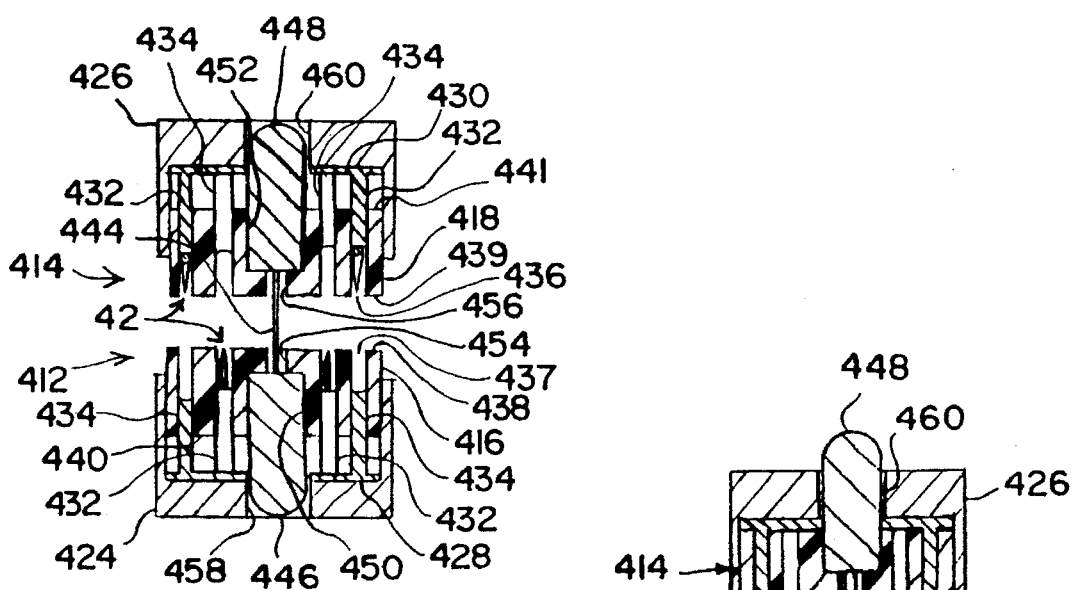
FIG. 34 is a cross-sectional view taken along line 34—34 in FIG. 33.
Figure 36:
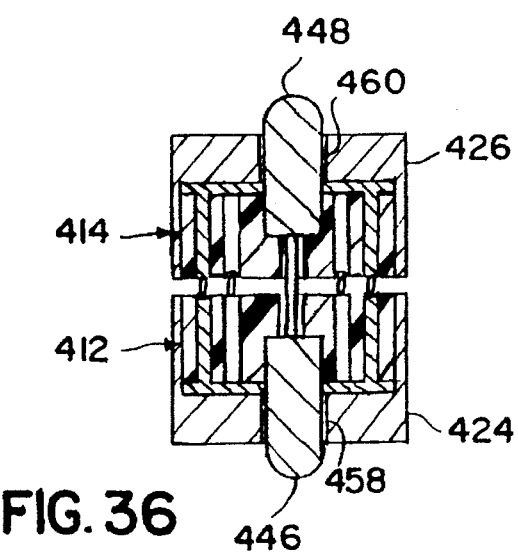
FIG. 36 is a cross-sectional view taken along line 36—36 in FIG. 35.
Figure 35:
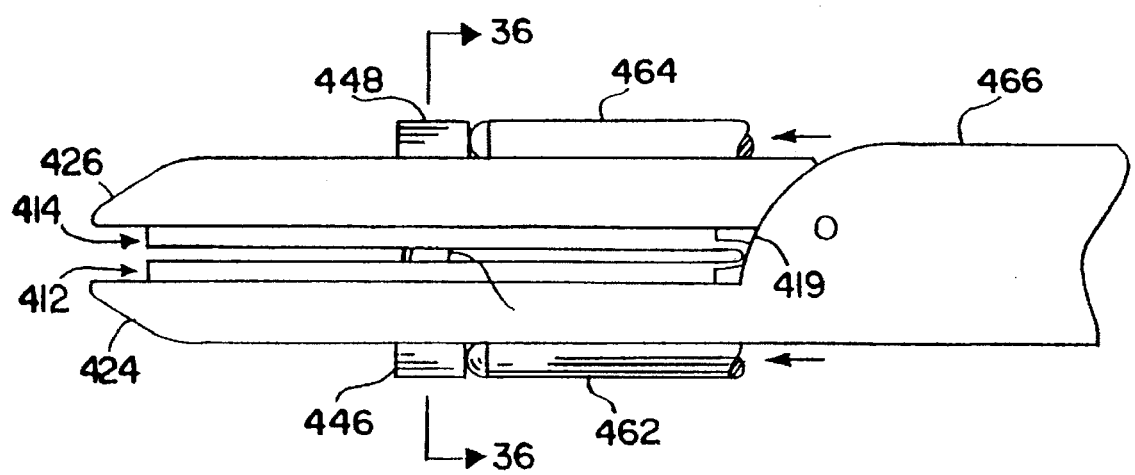
FIG. 35 is a side view illustrating use of the surgical stapler of FIG. 33.

With the jaws 424 and 426 of the stapler 410 opened, as shown in FIGS. 33 and 34, the knife blocks 446 and 448 extend between the rectangular grooves 450 and 452 into the slotted openings 458 and 460, respectively. With the stapler jaws 424 and 426 closed, as shown in FIGS. 35 and 36, the knife blocks 446 and 448 protrude outwardly from the slotted openings 458 and 460, respectively. A pair of movable pusher rods 462 and 464 are carried on the stapler housing 466 in longitudinal alignment with the protruding portions of knife blocks 446 and 448.

In use, the hinged staple cartridges 412 and 414 are inserted into opposed jaws 424 and 426 of the surgical stapler 410 and the jaws of the stapler 410 are positioned within an anatomical cavity. The biological tissue to be ligated is received between the opposed jaws 424 and 426 and cartridges 412 and 414 of the surgical stapler 410 with the knife blade 444 retracted proximally of the staple and anvil chambers 436 and 437. The jaws 424 and 426 are compressed against the biological tissue in the manner previously described, causing the cartridge bodies 416 and 418 to sink into the cavities 420 and 422, thereby applying staples from both sides of the tissue, and also causing the knife blocks 446 and 448 to protrude out of the slotted openings 458 and 460. With the tissue stapled and knife blocks 446 and 448 protruding, pusher rods 462 and 464 are advanced distally to bear against the protruding portions of the knife blocks 446 and 448 to cause distal movement of the blocks 446 and 448 within slotted openings 458 and 460 and the rectangular grooves 450 and 452. The knife blade 444 is carried along with the blocks 446 and 448 to cut between the finished rows of staples. The jaws 424 and 426 are then opened to expel the ligated tissue and the stapler 410 removed from the anatomical cavity for disposal or sterilization and reuse with a new pair of cartridges.

Figure 37:
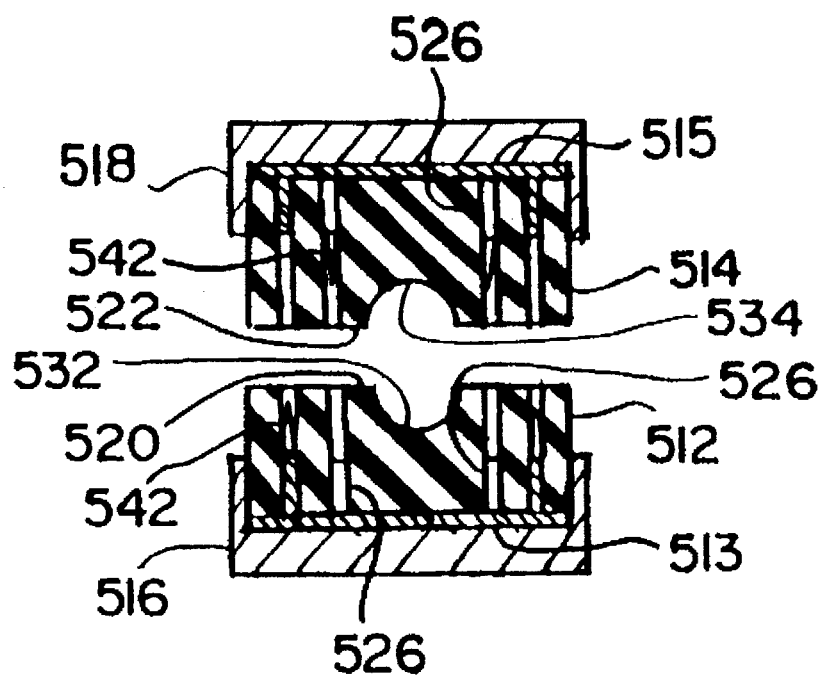
FIG. 37 is a cross-sectional end view of a surgical stapler according to the present invention taken through opposed jaws and compressible staple cartridges held therein.

In yet another modification of the surgical stapler of the present invention, shown in FIG. 37, a pair of compressible cartridge bodies 512 and 514 are frictionally held in opposed relation within cavities 513 and 515 formed in opposed jaws 516 and 518. Tissue engaging faces 520 and 522 of compressible cartridge bodies 512 and 514 extend above staples 542, staple drivers 524 and anvils 526 held in each cartridge, exposing the tissue penetrating legs of staples 542 to opposed anvils 526 only upon continued compression of the cartridge bodies 512 and 514 on opposite sides of the bodily tissue to be ligated. The cartridge bodies 512 and 514 can be made of any suitable, medically-acceptable material which is compressible, such as rubber, and other types of elastomers and can be solid, foamed or spongy. Peripheral edges of each cartridge are preferably unrestrained to allow lateral expansion during compression. To this end, central cavities 532 and 534 are also formed in the tissue engaging faces 520 and 522 between rows of staples 542 and anvils 526.

From the above, it will be appreciated that the surgical stapler of the present invention facilitates any surgical suturing procedure including ligation of vessels or ducts by applying rows of surgical staples from opposite sides of the biological tissue. By "ligation" is meant constricting or tying-off of any vessel or organ, and when used to ligate tissue, the stapler of the present invention receives the tissue between opposed jaws, pierces the tissue from opposite sides with tissue piercing legs of staples and bends the tissue piercing legs on opposed anvils. Thus, opposite sides of the tissue are held both by rows of crimped tissue penetrating legs and cross-members. It will also be appreciated that the surgical stapler of the present invention can be used to perform anastomosis. By "anastomosis" is meant the joining of adjacent hollow organs to permit communication therebetween, and when the stapler is used for anastomosis the jaws of the stapler are generally circular and each carry rings of staples and staple-forming anvils for positioning on opposite sides of the hollow organs to be joined.

Although the jaws of the present surgical stapler are opposed in use, the term "opposed" as used herein also encompasses jaws which are opposable and positioned in any manner relative to one another prior to being opposed. The jaws can be configured as desired to accommodate cartridges of any shape or size using any mechanism or structure suitable for retaining the cartridges within the jaws. Where movable jaws are provided, these jaws can hold staple cartridges which carry the anvils and staple drivers or one or both of the anvils and staple drivers can be formed directly on the jaws themselves. Any number of rows of staples can be applied from each of the opposed jaws, and these rows can be staggered, aligned or positioned in any other regular or irregular pattern relative one another. The staples are preferably conventional metal surgical staples, but can be made of any bioabsorbable or non-bioabsorbable material having suitable properties for producing deformable tissue penetrating legs. The tissue penetrating legs of the staples have been shown being bent inward for illustrative purposes; however, it will be appreciated that the legs could also be bent outward by increasing the lateral distance between indentations which make up the anvils, for example. In the case of curved jaws, the jaws can also hold cartridges that recede into cavities formed in the jaws, and staples held therein can be applied from one or both sides of the tissue being ligated. Additionally, any of the foregoing staple cartridges can be hinged together and provided as a single unitary piece to fit within the jaws of the stapler, and respective cartridge bodies can be rigid or semi-rigid for use with staple drivers or even elastic to expose the tissue penetrating legs of the staples by compression of the cartridge body.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of stapling biological tissue comprising the steps of positioning a first plurality of staples in at least two rows on a first side of the biological tissue to be stapled;

positioning a first plurality of staple-forming anvils in at least two rows on the first side of the biological tissue such that each row of staple-forming anvils is adjacent at least one row of staples;

positioning a second plurality of staples in at least two rows on a second side of the biological tissue in alignment with the first plurality of staple-forming anvils;

positioning a second plurality of staple-forming anvils in at least two rows on the second side of the biological tissue in alignment with the first plurality of staples;

piercing the biological tissue from the first side of the biological tissue with tissue piercing legs of the first plurality of staples;

piercing the biological tissue from the second side of the biological tissue with tissue piercing legs of the second plurality of staples;

bending the tissue piercing legs of the first plurality of staples against the second plurality of staple-forming anvils on the second side of the biological tissue;

bending the tissue piercing legs of the second plurality of staples against the first plurality of staple-forming anvils on the first side of the biological tissue; and cutting the biological tissue between the rows of staples such that at least two rows of staples extending through the biological tissue in opposite directions are disposed on each side of the cut.

2. A method as recited in claim 1 wherein said step of positioning a plurality of staples on first and second sides of the biological tissue includes placing the tissue between opposed jaws of a surgical stapler having a plurality of staples and staple-forming anvils carried by each jaw.

3. A method of stapling biological tissue as recited in claim 1 wherein said positioning steps include aligning at least one row of staple-forming anvils with interstices between a row of staples on the same side of the biological tissue.

4. A method of stapling biological tissue as recited in claim 1 wherein said positioning steps include aligning at least one row of staple-forming anvils with a row of staples on the same side of the biological tissue.

5. A method of stapling biological tissue as recited in claim 1 wherein each of the staples includes a pair of tissue piercing legs connected by a cross-member and said piercing step includes positioning a plurality a staple drivers on first and second sides of the biological tissue in engagement with the staple cross-members.

6. A method of stapling biological tissue as recited in claim 5 wherein said piercing step further includes supporting the staples and staple drivers in a pair of cartridges held within a pair of jaws and exposing tips of the tissue piercing legs of the staples by allowing the cartridges to recede into the jaws as the jaws are closed against the biological tissue.

7. A method of stapling biological tissue as recited in claim 5 wherein said piercing step further includes advancing a pair of pushers axially on opposite sides of the biological tissue to drive the staple-drivers.

8. A method of stapling biological tissue as recited in claim 1 wherein said positioning step includes arranging the staples and staple-forming anvils in spaced, parallel rows of linear configuration such that staple cross-members are oriented end-to-end in each row.

9. A method of stapling biological tissue as recited in claim 1 wherein said positioning step includes arranging the staples and staple-forming anvils in spaced rows of openly curved configuration such that opposite ends of each row do not meet to form a closed curved configuration.

* * * * *